United States Patent
Li et al.

(10) Patent No.: US 10,153,438 B2
(45) Date of Patent: Dec. 11, 2018

(54) ORGANIC LIGHT-EMITTING DEVICE

(71) Applicant: KYULUX, INC., Fukuoka-shi, Fukuoka (JP)

(72) Inventors: Jie Li, Fukuoka (JP); Qisheng Zhang, Fukuoka (JP); Hiroko Nomura, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 15/304,973

(22) PCT Filed: Apr. 17, 2015

(86) PCT No.: PCT/JP2015/061831
§ 371 (c)(1),
(2) Date: Oct. 18, 2016

(87) PCT Pub. No.: WO2015/159971
PCT Pub. Date: Oct. 22, 2015

(65) Prior Publication Data
US 2017/0229658 A1 Aug. 10, 2017

Related U.S. Application Data

(60) Provisional application No. 61/981,368, filed on Apr. 18, 2014.

(51) Int. Cl.
H01L 51/50 (2006.01)
H01L 51/00 (2006.01)
(Continued)

(52) U.S. Cl.
CPC ........ H01L 51/0072 (2013.01); C07D 487/16 (2013.01); C09K 11/025 (2013.01);
(Continued)

(58) Field of Classification Search
None
See application file for complete search history.

(56) References Cited

U.S. PATENT DOCUMENTS

| 6,602,618 B2 * | 8/2003 | Watanabe | ........... H01L 51/0081 313/504 |
| 2012/0091884 A1 * | 4/2012 | Macdonald | .......... C07D 487/16 313/504 |

FOREIGN PATENT DOCUMENTS

| CN | 102317408 | 1/2012 |
| JP | 2012-518285 | 8/2012 |

(Continued)

OTHER PUBLICATIONS

Li, et al., Highly efficient exciplex organic light-emitting diodes incorporating a heptazine derivative as an electron acceptor, Chem. Commun., 2014, pp. 6174-6176, vol. 50.

(Continued)

Primary Examiner — Gregory D Clark
(74) Attorney, Agent, or Firm — Browdy and Neimark, PLLC

(57) ABSTRACT

An organic light-emitting device containing a compound having a lone electron pair and a π electron orbital, the compound emitting fluorescent light by such a mechanism that when at least a part of electrons constituting the lone electron pair is excited to an excited triplet state $^3n\pi^*$ through $n\pi^*$ transition, the part of electrons undergoes inverse intersystem crossing from the excited triplet state $^3n\pi^*$ to an excited singlet state $^1n\pi^*$, and returns from the excited singlet state $^1n\pi^*$ to the ground state, at which the fluorescent light is emitted. The organic light-emitting device has a high light emission efficiency.

21 Claims, 4 Drawing Sheets

(51) Int. Cl.
  *C09K 11/02* (2006.01)
  *C09K 11/06* (2006.01)
  *C07D 487/16* (2006.01)
(52) U.S. Cl.
  CPC ...... *C09K 11/06* (2013.01); *C09K 2211/1007* (2013.01); *C09K 2211/1074* (2013.01); *H01L 51/5012* (2013.01); *H01L 51/5028* (2013.01); *H01L 2251/552* (2013.01)

(56) References Cited

FOREIGN PATENT DOCUMENTS

| JP | 2012-527744 | 11/2012 |
| JP | 5366106 | 12/2013 |
| WO | 2010/132953 | 11/2010 |
| WO | 2013/133359 | 9/2013 |

OTHER PUBLICATIONS

Notification of Transmittal of copies of Translation of the International preliminary report on patentability (Chapter I or II) from international application No. PCT/JP2015/061831, dated Oct. 27, 2016.
Notification Concerning Transmittal of International preliminary report on patentability (Chapter I of the Patent Corporation Treaty) from international application No. PCT/JP2015/061831, dated Oct. 27, 2016.
Chinese office action with translation dated Sep. 4, 2017 from corresponding Chinese application No. 201580019638.2.
Office Action for corresponding Chinese Patent Application No. 201580019638.2, dated May 4, 2018, with English Machine translation.
Tetsuya et al., Highly Efficient Organic Light-Emitting Diode Based on a Hidden Thermally Activated Delayed Fluorescence Channel in Heptazine Derivative, Adv. Mater., pp. 1-5 (2013).

* cited by examiner

HOMO　　　　　LUMO

ORGANIC LIGHT-EMITTING DEVICE

TECHNICAL FIELD

The present invention relates to an organic light-emitting device, such as an organic electroluminescent device.

BACKGROUND ART

An organic light-emitting device, such as an organic electroluminescent device (organic EL device), has been actively studied for enhancing the light emission efficiency thereof. In particular, various studies for enhancing the light emission efficiency have been made by newly developing and combining an electron transporting material, a hole transporting material, a light-emitting material and the like constituting an organic electroluminescent device. Among the studies, for developing a light-emitting material having a highs light emission efficiency, extensive studies have been made from various standpoints.

In recent years, among fluorescent materials, particularly, a delayed fluorescent material emitting delayed fluorescent light is receiving attention. Delayed fluorescent light is fluorescent light that is emitted by utilizing the inverse intersystem crossing from the excited triplet state to the excited singlet state, and is observed as fluorescent light that has a longer lifetime than normal fluorescent light. By producing an organic electroluminescent device using the delayed fluorescent material, a light emission efficiency that exceeds the theoretical limit in the use of a normal fluorescent material can be achieved. Accordingly, delayed fluorescent materials having various structures have been developed. (see, for example, PTL 1).

CITATION LIST

Patent Literatures

PTL 1: Japanese Patent No. 5,366,106

SUMMARY OF INVENTION

Technical Problem

It has been known from the past studies that the materials emitting delayed fluorescent light have some common conditions. For example, it has been known that the molecular design, in which a donor moiety and an acceptor moiety are present in the molecule, and the overlap of the HOMO (highest occupied molecular orbital) and the LUMO (lowest unoccupied molecular orbital) is small, facilitates the provision of a novel delayed fluorescent material. However, the development researches of the delayed fluorescent material based on the conventional knowledge can provide only delayed fluorescent materials within the range that is expected and understood from the conventional knowledge. Accordingly, there is a demand of the development of a delayed fluorescent material from the standpoint that exceeds the conventional knowledge, and the provision of an organic light-emitting device capable of achieving a higher light emission efficiency utilizing the material. The present inventors have made earnest investigations for developing a delayed fluorescent material based on the new standpoint.

Solution to Problem

As a result of the investigations made by the inventors, the inventors have succeeded to develop an organic light-emitting device capable of achieving a high light emission efficiency through a novel mechanism, and the invention including the following embodiments has been completed.

[1] An organic light-emitting device containing a compound having a lone electron pair and a π electron orbital, the compound emitting fluorescent light by such a mechanism that when at least a part of electrons constituting the lone electron pair is excited to an excited triplet state $^3n\pi^*$ through $n\pi^*$ transition, the part of electrons undergoes inverse intersystem crossing from the excited triplet state $^3n\pi^*$ to an excited singlet state $^1n\pi^*$, and returns from the excited singlet state $^2n\pi^*$ to the ground state, at which the fluorescent light is emitted.

[2] The organic light-emitting device according to the item [1], wherein the compound has an energy level of the excited triplet state $^3n\pi^*$ through $n\pi^*$ transition that is lower than an energy level of an excited triplet state $^3\pi\pi^*$ through $\pi\pi^*$ transition.

[3] The organic light-emitting device according to the item [1] or [2], wherein the compound has a difference in energy between the excited triplet state $^3n\pi^*$ and the excited singlet state $^1n\pi^*$ that is smaller than a difference in energy between the excited triplet state $^3n\pi^*$ and the ground state.

[4] The organic light-emitting device according to any one of the items [1] to [3], wherein the compound contains a nitrogen atom.

[5] The organic light-emitting device according to the item [4], wherein the compound has a heteroaromatic ring containing a nitrogen atom.

[6] The organic light-emitting device according to the item [5], wherein the compound is a derivative of heptazine.

[7] The organic light-emitting device according to the item [6], wherein the compound is a compound represented by the following general formula (1):

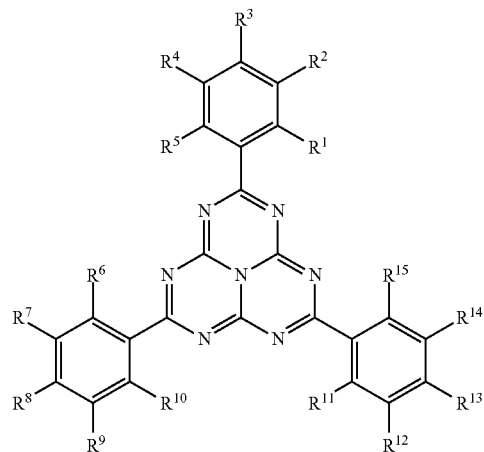

General Formula (1)

wherein in the general formula (1), $R^1$ to $R^{15}$ each independently represent, a hydrogen atom or a substituent, provided that at least one of $R^1$ to $R^5$, at least one of $R^6$ to $R^{10}$, and at least one of to $R^{11}$ to $R^{15}$ each independently represent a halogen atom, at least one of the balance of $R^1$ to $R^5$, at least one of the balance of $R^6$ to $R^{10}$, and at least one of the balance of $R^{11}$ to $R^{15}$ each independently represent an alkyl group, and $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

[8] The organic light-emitting device according to any one of the items [1] to [7], wherein the light-emitting device contains a pair of electrodes, and an organic layer including a light-emitting layer provided between the pair of electrodes, and
the compound is contained at least in the light-emitting layer.

[9] The organic light-emitting device according to the item [8], wherein the light-emitting layer contains a light-emitting dopant, an assist dopant, and a host, and the compound is used as the assist dopant.

[10] An organic light-emitting device containing a compound represented by the following general formula (1):

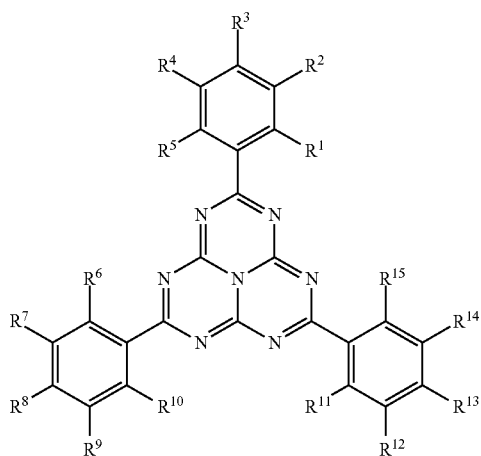

General Formula (1)

wherein in the general formula (1), $R^1$ to $R^{15}$ each independently represent a hydrogen atom or a substituent, provided that at least one of $R^1$ to $R^5$, at least one of $R^6$ to $R^{10}$, and at least one of $R^{11}$ to $R^{15}$ each independently represent a halogen atom, at least one of the balance of $R^1$ to $R^5$, at least one of the balance of $R^6$ to $R^{10}$, and at least one of the balance of $R^{11}$ to $R^{15}$ each independently represent an alkyl group, and $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

[11] The organic light-emitting device according to the item [10], wherein in the general formula (1), any one of $R^1$ to $R^5$, any one of $R^6$ to $R^{10}$, and any one of $R^{11}$ to $R^{15}$ each independently represent a halogen atom, and any one of the balance of $R^1$ to $R^5$, any one of the balance of $R^6$ to $R^{10}$, and any one of the balance of $R^{11}$ to $R^{15}$ each independently represent an alkyl group.

[12] The organic light-emitting device according to the item [10] or [11], wherein the substitution position of the alkyl group on the benzene ring is an o-position with respect to the substitution position of the halogen atom.

[13] The organic light-emitting device according to any one of the items [10] to [12], wherein in the general formula (1), $R^3$, $R^8$, and $R^{13}$ each independently represent a halogen atom.

[14] The organic light-emitting device according to the item [13], wherein in the general formula (1), $R^2$, $R^7$, and $R^{12}$ each independently represent an alkyl group.

[15] The organic light-emitting device according to any one of the items [10] to [14], wherein the halogen atom is a fluorine atom.

[16] The organic light-emitting device according to any one of the items [10] to [15], wherein the alkyl group is a methyl group.

[17] The organic light-emitting device according to any one of the items [10] to [16], wherein $R^1$ to $R^{15}$ that do not represent a halogen atom or an alkyl group represent hydrogen atoms.

[18] The organic light-emitting device according to any one of the items [10] to [17], wherein the organic light-emitting device emits delayed fluorescent light.

[19] The organic light-emitting device according to any one of the items [10] to [18], wherein the organic light-emitting device is an organic electroluminescent device.

[20] The organic light-emitting device according to the item [19], wherein the organic light-emitting device contains a pair of electrodes, and an organic layer including a light-emitting layer provided between the pair of electrodes, and
the compound represented by the general formula (1) is contained at least in the light-emitting layer.

[21] The organic light-emitting device according to any one of the items [1] to [20], wherein the compound has a fluorescence lifetime of 1 μs or less.

[22] An assist dopant containing the compound according to any one of the items [1] to [21].

Advantageous Effects of Invention

The organic light-emitting device of the invention efficiently emits fluorescent radiation from $^1n\pi^*$ by utilizing the $n\pi^*$ transition and the inverse intersystem crossing, and is a light-emitting device of a novel type beyond the conventional technical common knowledge.

DESCRIPTION OF EMBODIMENTS

Figure 1:
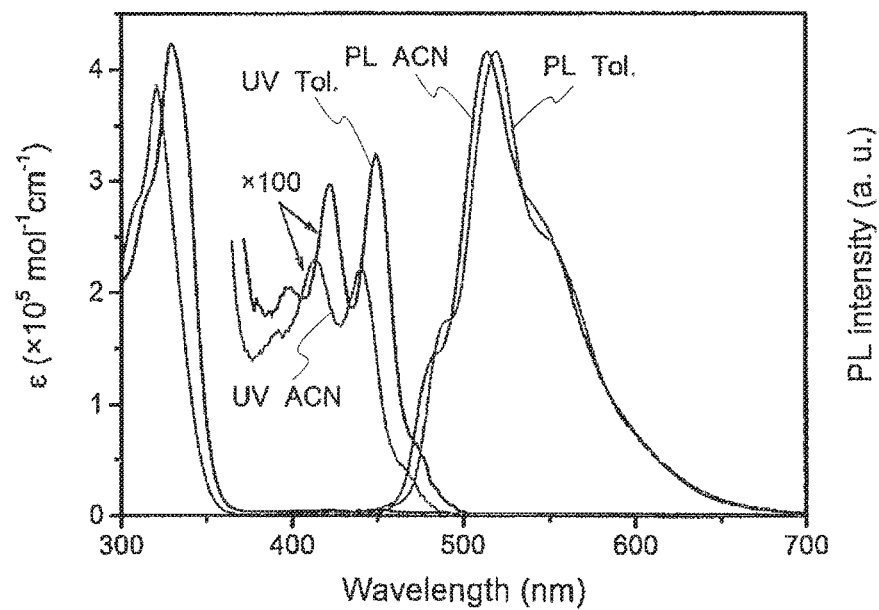
FIG. 1 shows the ultraviolet-visible absorption spectra and the light emission spectra of the toluene solution and the acetonitrile solution of the compound 1 in Example.

The contents of the invention will be described in detail below. The constitutional elements may be described below with reference to representative embodiments and specific examples of the invention, but the invention is not limited to the embodiments and the examples In the description, a numerical range expressed with reference to an upper limit and/or a lower limit means a range that includes the upper limit and/or the lower limit. In the invention, the hydrogen atom that is present in the molecule of the compound used in the invention is not particularly limited in isotope species, and for example, all the hydrogen atoms in the molecule may be $^1$H, and all or a part of them may be $^2$H (deuterium (D)).

Features of Organic Bight-Emitting Device

The organic light-emitting device of the invention uses a compound having a lone electron pair and a π electron orbital. The compound having a lone electron pair and a π electron orbital used in the invention emits fluorescent light by such a mechanism that when at least a part of electrons constituting the lone electron pair is excited to an excited triplet state $^3$nπ* through nπ* transition, the part of electrons undergoes inverse intersystem crossing from the excited triplet state $^3$nπ* to an excited singlet state $^1$nπ*, and returns from the excited singlet state $^1$nπ* to the ground state, at which the fluorescent light is emitted.

The effect of enhancing the fluorescent light emission efficiency through inverse intersystem crossing will be described for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. Among the materials, a thermal activation type delayed fluorescent material emitting light through absorption of thermal energy is particularly useful for an organic electroluminescent device in the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus delayed fluorescent light is observed as fluorescent light that is delayed from the normal fluorescent light and phosphorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency. In the invention, when an excited triplet state $^3$nπ* is formed through nπ* transition, the excited triplet state $^3$nπ* undergoes inverse intersystem crossing to an excited singlet state $^1$nπ*, and the excited singlet state $^1$nπ* returns to the ground state, at which the fluorescent light is efficiently emitted.

Compound

The compound used in the invention has a lone electron pair and a π electron orbital, and emits fluorescent light by such a mechanism that when an excited triplet state $^3$nπ* is formed through nπ* transition, the excited triplet state $^3$nπ* undergoes inverse intersystem crossing to an excited singlet state $^1$nπ*, and the excited singlet state $^1$nπ* returns to the ground state, at which the fluorescent light is emitted. In the following description, the compound of this type will be described by referring to as an nπ* type compound. The structure of the nπ* type compound used in the invention is not particularly limited, as far as the compound has the aforementioned properties.

The difference in energy (ΔE) between the excited singlet state $^1$nπ* and the excited triplet state $^3$nπ* of the nπ* type compound is preferably less than 0.3 eV, more preferably less than 0.2 eV, further preferably less than 0.15 eV, and particularly preferably less than 0.1 eV. The energy difference between the excited singlet state $^1$nπ* and the ground state of the nπ* type compound is preferably such a difference in energy that is capable of emitting fluorescent radiation having a wavelength of from 360 to 800 nm. Examples of the compound used include a compound having a difference in energy that is capable of emitting fluorescent radiation having a wavelength of from 360 to 540 nm, and a compound having a difference in energy that is capable of emitting fluorescent radiation having a wavelength of from 500 to 540 nm.

The nπ* type compound used in the invention is preferably a compound containing a nitrogen atom, more preferably a compound having a heteroaromatic ring containing a nitrogen atom, and further preferably a compound having a polycyclic structure containing a heteroaromatic ring containing a nitrogen atom fused. Examples of the compound include a heptazine derivative having a heptazine ring.

The nπ* type compound used in the invention may not be necessarily a compound having a donor moiety and an acceptor moiety in the molecule thereof. The donor moiety referred herein means an atom or an atomic group having a Hammett σp value of −0.2 or less, and the acceptor moiety referred herein means an atom or an atomic group having a Hammett σp value of 0.2 or more. For the Hammett σp values used herein, the values described in Jerry March, Advanced Organic Chemistry, McGraw-hill International Book Co. may be employed. Accordingly, in the invention, a compound that does not have an atom or an atomic group having a Hammett σp value of −0.2 or less (i.e., a donor moiety), a compound that does not have an atom or an atomic group having a Hammett σp value of 0.2 or more (i.e., an acceptor moiety), and a compound that does not have both an atom or an atomic group having a Hammett σp value of −0.2 or less (i.e., a donor moiety) and an atom or an atomic group having a Hammett σp value of 0.2 or more (i.e., an acceptor moiety) can be used. Furthermore, in the invention, a compound that does not have an atom or an atomic group having a Hammett σp value of −0.1 or less, a compound that does not have an atom or an atomic group having a Hammett σp value of 0.1 or more, a compound that does not have both an atom or an atomic group having a Hammett σp value of −0.1 or less and an atom or an atomic group having a Hammett σp value of 0.1 or more can be used.

Preferred examples of the nπ* type compound that can be used in the invention include a compound represented by the following general formula (1).

General Formula (1)

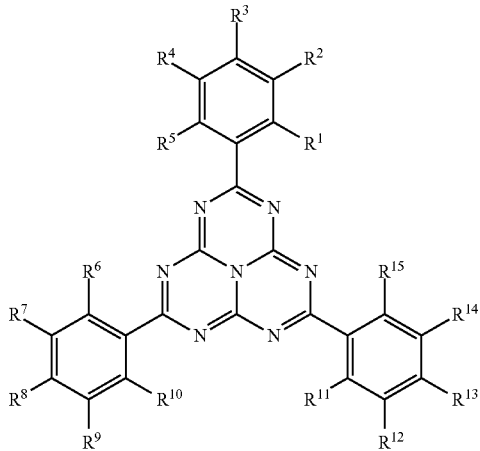

In the general formula (1), $R^1$ to $R^{15}$ each independently represent a hydrogen atom or a substituent, provided that at least one of $R^1$ to $R^5$, at least one of $R^6$ to $R^{10}$, and at least one of $R^{11}$ to $R^{15}$ each independently represent a halogen atom, at least one of the balance of $R^1$ to $R^5$, at least one of the balance of $R^6$ to $R^{10}$, and at least one of the balance of $R^{11}$ to $R^{15}$ each independently represent an alkyl group, and $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

Examples of the substituent represented by $R^1$ to $R^{15}$ include a substituted or unsubstituted alkyl group, a substituted or unsubstituted aryl group, a substituted or unsubstituted heteroaryl group, a substituted or unsubstituted alkoxy group, a substituted or unsubstituted aryloxy group, a substituted or unsubstituted heteroaryloxy group, and a halogen atom. Among these, a substituted or unsubstituted alkyl group and a halogen atom are preferably used.

The substituent represented by $R^1$ to $R^{15}$ is also preferably selected from an atom or an atomic group having a Hammett σp value in a range of from −0.2 to 0.2 in this case, the kind of the substituent represented by $R^1$ to $R^{15}$ is not particularly limited.

The alkyl group referred herein may be linear, branched, or cyclic. A linear or branched alkyl group is preferred. The number of carbon atoms of the alkyl group is preferably from 1 to 20, more preferably from 1 to 12, further preferably from 1 to 6, and still further preferably from 1 to 3 (i.e., a methyl group, an ethyl group, an n-propyl group, and an isopropyl group). Examples of the cyclic alkyl group include a cyclopentyl group, a cyclohexyl group, and a cycloheptyl group.

The aryl group referred herein may contain one aromatic ring or may have a structure having two or more aromatic rings fused to each other. The number of carbon atoms of the aryl group is preferably from 6 to 22, more preferably from 6 to 18, further preferably from 6 to 14, and still further preferably from 6 to 10 (i.e., a phenyl group, a 1-naphthyl group, and a 2-naphthyl group).

The heteroaryl group referred herein may contain one ring or may have a structure having two or more aromatic rings fused to each other. The number of carbon atoms of the heteroaryl group is preferably from 3 to 21, more preferably from 3 to 17, further preferably from 3 to 13, and still further preferably from 3 to 9.

The alkoxy group referred herein may be linear, branched, or cyclic. A linear or branched alkoxy group is preferred. The number of carbon atoms of the alkoxy group is preferably from 1 to 20, more preferably from 1 to 12, further preferably from 1 to 6, and still further preferably from 1 to 3 (i.e., a methoxy group, an ethoxy group, an n-propoxy group, and an isopropoxy group). Examples of the cyclic alkoxy group include a cyclopentyloxy group, a cyclohexyloxy group, and a cycloheptyloxy group.

The aryloxy group referred herein may contain one aromatic ring or may have a structure having two or more aromatic rings fused to each other. The number of carbon atoms of the aryloxy group is preferably from 6 to 22, more preferably from 6 to 18, further preferably from 6 to 14, and still further preferably from 6 to 10 (i.e., a phenyloxy group, a 1-naphthyloxy group, and a 2-naphthyloxy group).

The heteroaryloxy group referred herein may contain one ring or may have a structure having two or more aromatic rings fused to each other. The number of carbon atoms of the heteroaryloxy group is preferably from 3 to 21, more preferably from 3 to 17, further preferably from 3 to 13, and still further preferably from 3 to 9.

The alkyl group, the aryl group, the heteroaryl group, the alkoxy group, the aryloxy group, and the heteroaryloxy group that may be represented by $R^1$ to $R^{15}$ each may be further substituted. In the case where the group is substituted, examples of the substituent include an alkyl group, an aryl group, a heteroaryl group, an alkoxy group, an aryloxy group, a heteroaryloxy group, and a halogen atom.

The halogen atom referred herein is preferably a fluorine atom, a chlorine atom, a bromine atom, or an iodine atom, more preferably a fluorine atom, a chlorine atom, or a bromine atom, further preferably a fluorine atom or a chlorine atom, and particularly preferably a fluorine atom.

In the general formula (1), at least one of $R^1$ to $R^5$, at least one of $R^6$ to $R^{10}$, and at least one of $R^{11}$ to $R^{15}$ each independently represent a halogen atom. Preferred examples include a case where at least $R^3$ in $R^1$ to $R^5$, at least $R^8$ in $R^6$ to $R^{10}$, and at least $R^{13}$ in $R^{11}$ to $R^{15}$ each represent a halogen atom. Preferred examples also include a case where at least $R^2$ in $R^1$ to $R^5$, at least $R^7$ in $R^6$ to $R^{10}$, and at least $R^{12}$ in $R^{11}$ to $R^{15}$ each represent a halogen atom. Preferred examples also include a case where only $R^3$ in $R^1$ to $R^5$, only $R^8$ in $R^6$ to $R^{10}$, and only $R^{13}$ in $R^{11}$ to $R^{15}$ each represent a halogen atom.

In the general formula (1), at least one of the balance of $R^1$ to $R^5$, at least one of the balance of $R^6$ to $R^{10}$, and at least one of the balance of $R^{11}$ to $R^{15}$ each independently represent an alkyl group. The "balance" referred herein means that the "other ones than the halogen atoms". Preferred examples include a case where at least $R^2$ in $R^1$ to $R^5$, at least $R^7$ in $R^6$ to $R^{10}$, and at least $R^{12}$ in $R^{11}$ to $R^{15}$ each represent an alkyl group. Preferred examples also include a case where at least $R^3$ in $R^1$ to $R^5$, at least $R^8$ in $R^6$ to $R^{10}$, and at least $R^{13}$ in $R^{11}$ to $R^{15}$ each represent an alkyl group.

Examples of one preferred embodiment of the general formula (1) include an embodiment, in which any one of $R^1$ to $R^5$, any one of $R^6$ to $R^{10}$, and any one of $R^{11}$ to $R^{15}$ each independently represent a halogen atom, and at least one of the balance of $R^1$ to $R^5$, at least one of the balance of $R^6$ to $R^{10}$, and at least one of the balance of $R^{11}$ to $R^{15}$ each independently represent an alkyl group.

Examples of one preferred embodiment of the general formula (1) also include an embodiment, in which any one of $R^1$ to $R^5$, any one of $R^6$ to $R^{10}$, and any one of $R^{11}$ to $R^{15}$ each independently represent a halogen atom, and any one of the balance of $R^1$ to $R^5$, any one of the balance of $R^6$ to $R^{10}$, and any one of the balance of $R^{11}$ to $R^{15}$ each independently represent an alkyl group.

The substitution position of the alkyl group on the benzene ring is preferably the o-position with respect to the substitution position of the halogen atom. In other words, the carbon atom of the benzene ring bonded to the halogen atom and the carbon atom of the benzene ring bonded to the alkyl group are preferably on positions adjacent to each other. Specifically, $R^3$, $R^8$, and $R^{13}$ in the general formula (1) each preferably independently represent a halogen atom, and $R^2$, $R^7$, and $R^{12}$ in the general formula (1) each preferably independently represent an alkyl group.

Examples of the combination of the halogen atom and the alkyl group each bonded to the benzene rings in the general formula (1) include a combination of a fluorine atom and a methyl group, a combination of a fluorine atom and an ethyl group, and a combination of a fluorine atom and a propyl group.

The benzene rings in the general formula (1) each may be substituted with a substituent other than the halogen atom and the alkyl group, or may not be substituted. For example, only the halogen atom and the alkyl group may be substituted on the benzene rings, and hydrogen atoms may be bonded to the other positions.

In the general formula (1), $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure. The cyclic structure referred herein may be an aromatic ring or an aliphatic ring, and may be a structure containing a hetero atom, and the cyclic structure may be a condensed ring containing two or more rings. The hetero atom referred herein is preferably selected from the group consisting of a nitrogen atom, an oxygen atom, and a sulfur atom, more preferably a nitrogen atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, and a cycloheptaene ring.

The synthesis method of the compound represented by the general formula (1) is not particularly limited. The compound represented by the general formula (1) may be synthesized by combining the known synthesis methods and conditions. For example, the compound may be synthesized by appropriately selecting, combining, and modifying the synthesis methods described in paragraphs 0039 to 0049 of JP-A-2009-501194. The compound represented by the general formula (1) may be synthesized by combining the other known synthesis reactions.

Structure of Organic Light-Emitting Device

The organic light-emitting device of the invention contains the $n\pi^*$ type compound having a lone electron pair and a $\pi$ electron orbital. As described above, the $n\pi^*$ type compound is a compound that emits fluorescent light by such a mechanism that when at least a part of electrons constituting the lone electron pair is excited to an excited triplet state $^3n\pi^*$ through $n\pi^*$ transition, the part of electrons undergoes inverse intersystem crossing from the excited triplet state $^3n\pi^*$ to an excited singlet state $^1n\pi^*$, and returns from the excited singlet state $^1n\pi^*$ to the ground state, at which the fluorescent light is emitted.

The organic light-emitting device of the invention may be constituted in such a manner that the fluorescent light emitted from the $n\pi^*$ type compound is directly radiated outside. In other words, the $n\pi^*$ type compound may be used as a light-emitting material. At this time, the $n\pi^*$ type compound contained in the organic light-emitting device is considerably enhanced in fluorescent light emission efficiency on returning from $^1n\pi^*$ to the ground state due to the inverse intersystem crossing. Accordingly, although it has been unable to observe fluorescent light on returning from $^1n\pi^*$ to the ground state with a practical light emission intensity particularly under a temperature condition of 20° C. or more, the invention enables emission of fluorescent light on returning from $^1n\pi^*$ to the ground state with a higher light emission efficiency. According to the invention, for example, an organic electroluminescent device having an external quantum efficiency of 3% or more, 5% or more, or 6% or more can be provided.

In the organic light-emitting device of the invention, the $n\pi^*$ type compound may also be used as an assist dopant. In other words, the $n\pi^*$ type compound may have a function of assisting the light emission of the light-emitting material contained in the light-emitting layer. At this time, the $n\pi^*$ type compound contained in the light-emitting layer may have a lowest excited singlet energy level that is between the lowest excited singlet energy level of the host material contained in the light-emitting layer and the lowest excited singlet energy level of the light-emitting material contained in the light-emitting layer. In the case where the $n\pi^*$ type compound having a short fluorescence lifetime is used, the $n\pi^*$ type compound can be preferably used as an assist dopant. For example, an embodiment, in which the $n\pi^*$ type compound having a fluorescence lifetime of 1 μs or less is used as an assist dopant, may be exemplified.

The organic electroluminescent device has a structure containing at least an anode, a cathode, and an organic layer formed between the anode and the cathode. The organic layer contains at least a light-emitting layer, and may be formed only of a light-emitting layer, or may have one or more organic layer in addition to the light-emitting layer. Examples of the organic layer include a hole injection layer, a hole transporting layer, an electron barrier layer, a hole barrier layer, an electron transporting layer, an electron injection layer, and an exciton barrier layer. The hole transporting layer may be a hole injection and transporting layer having a hole injection function, and the electron transporting layer may be an electron injection and transporting layer having an electron injection function.

The members and the layers of the organic electroluminescent device will be described below.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more) the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material.

The light-emitting material used may be one kind or two or more kinds of the $n\pi^*$ type compound. In order that the organic light-emitting device of the invention exhibits a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation in the organic light-emitting device of the invention, the light emission occurs in the light-emitting material contained in the light-emitting layer. The emitted light may contain both fluorescent light and delayed fluorescent light. However, a part of the emitted light may contain emitted light from the host material, or the emitted light may partially contain emitted light from the host material.

In the case where the host material is used, the amount of the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the nπ* type compound may be used not only in the light-emitting layer but also in the other layers than the light-emitting layer. In this case, the nπ* type compound used in the light-emitting layer and the nπ* type compound used in the other layers than the light-emitting layer may be the same as or different from each other. For example, the nπ* type compound may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_1$ to $R_{10}$ each independently represent a hydrogen atom or a substituent, and n represents an integer of from 3 to 5.

Preferred examples of a compound that may also be used as the host material of the light-emitting layer are shown below.

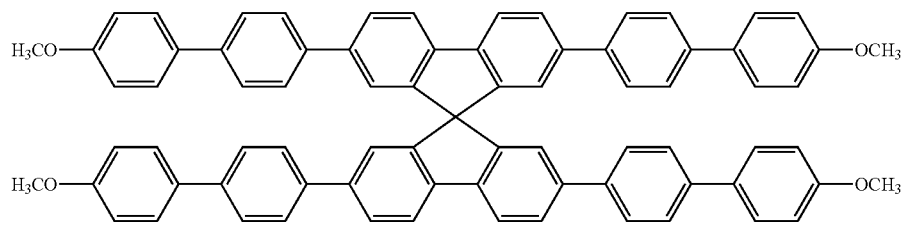

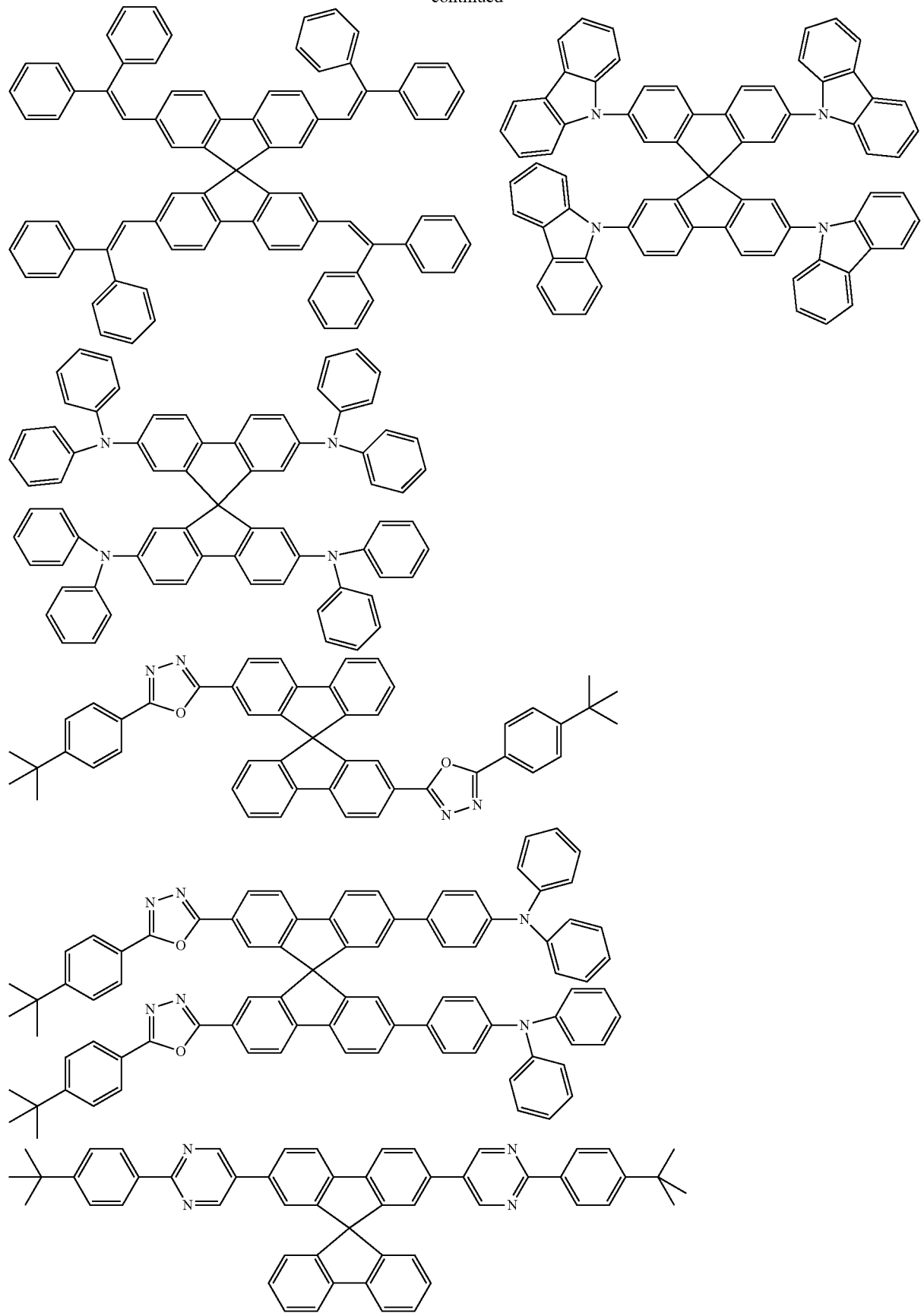

-continued
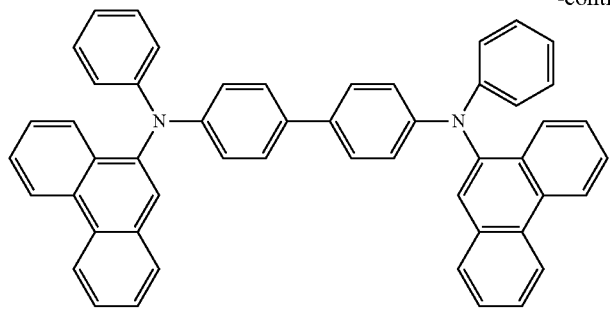
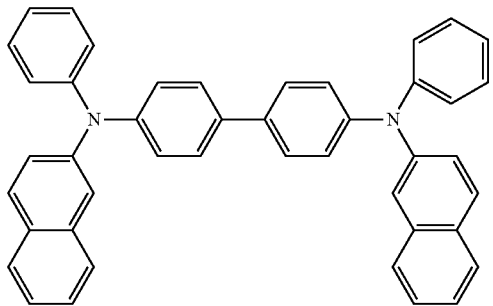
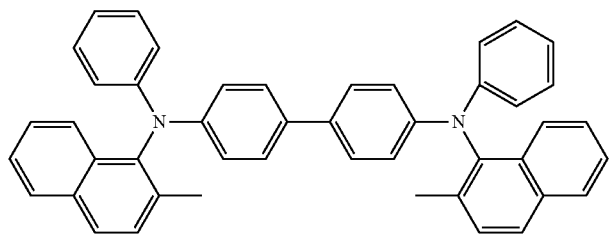
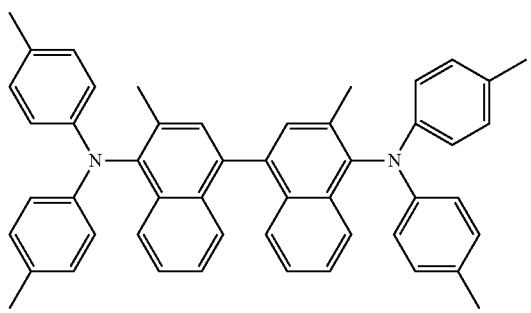
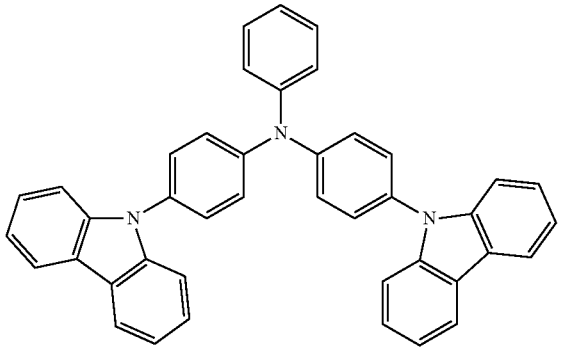
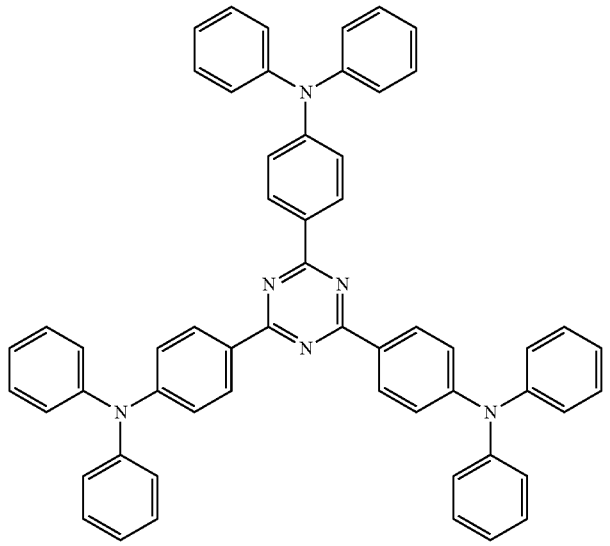
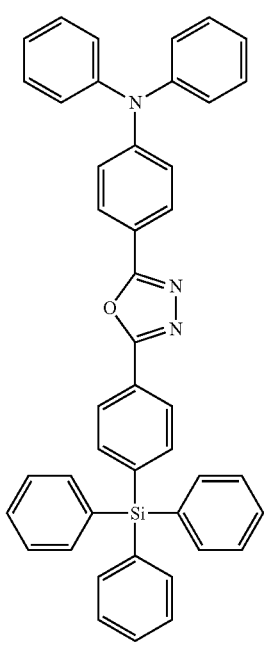

-continued
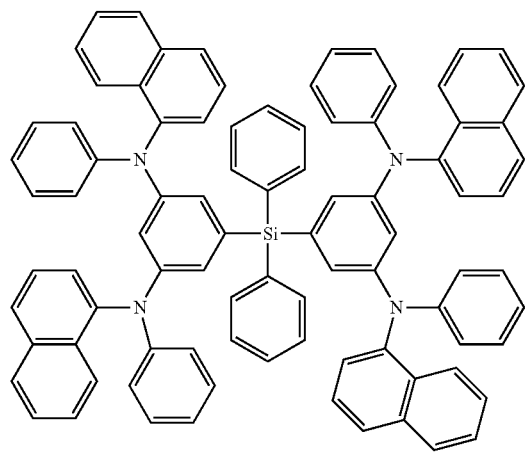
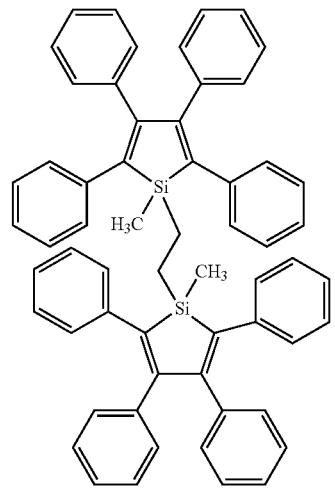
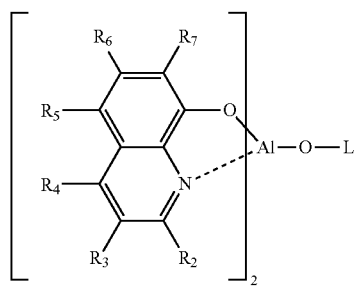
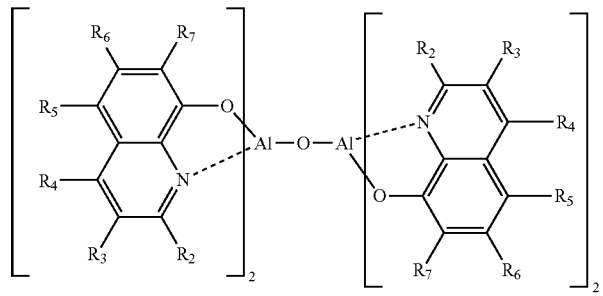
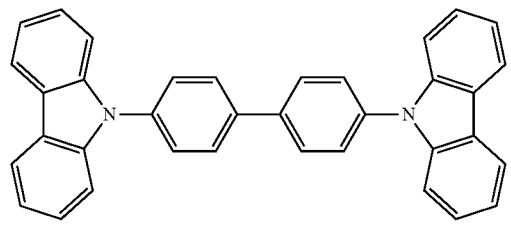
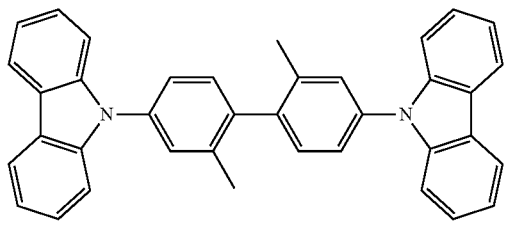
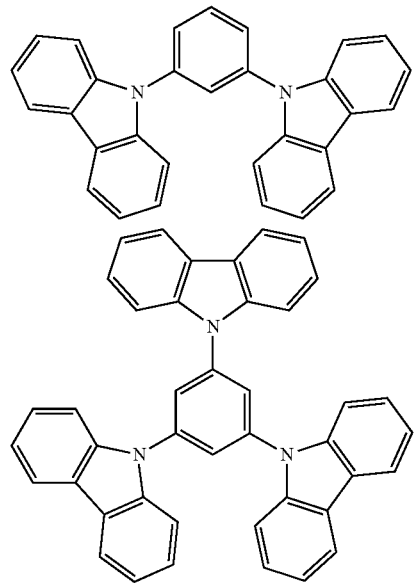
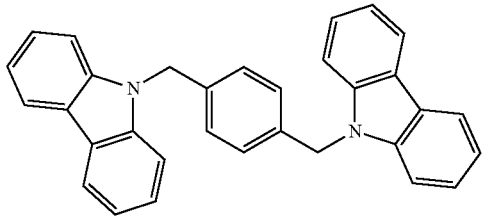
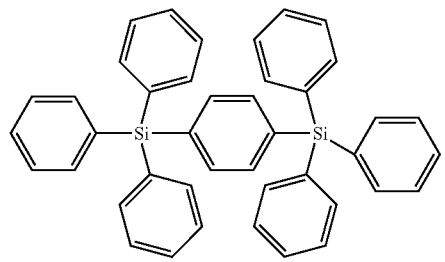

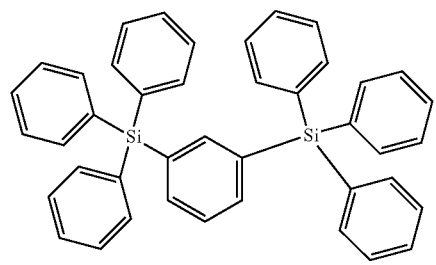
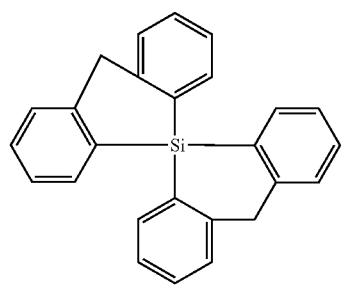
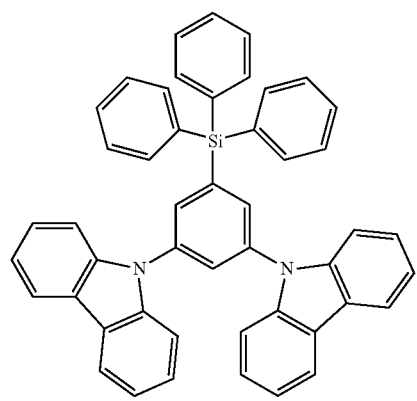
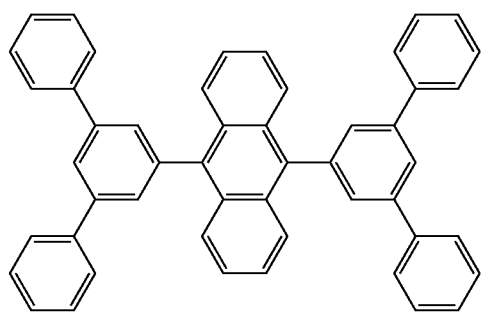
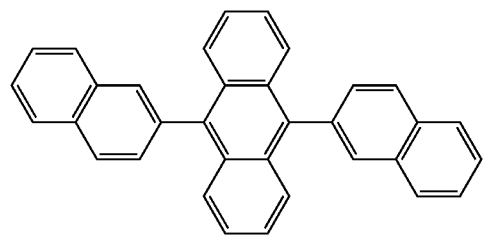
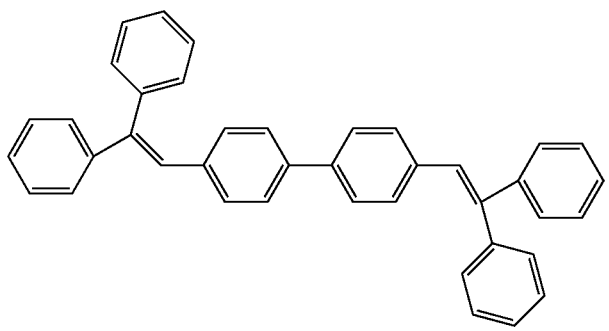
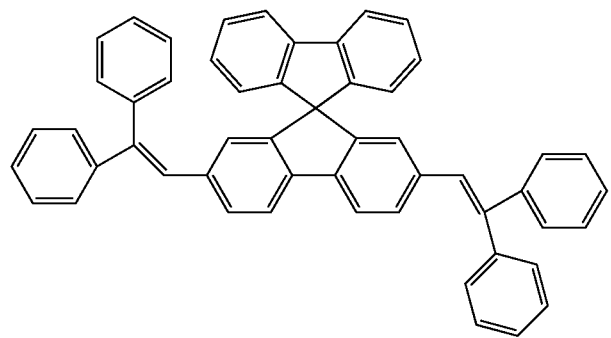
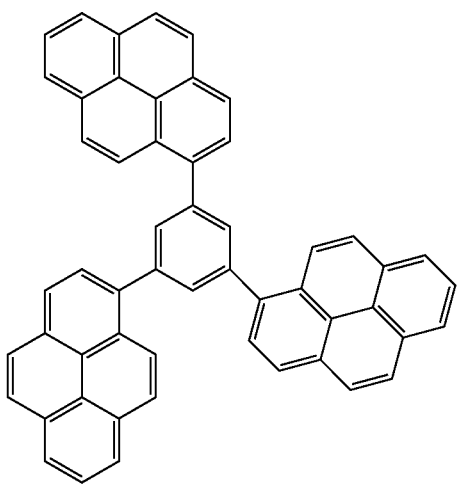

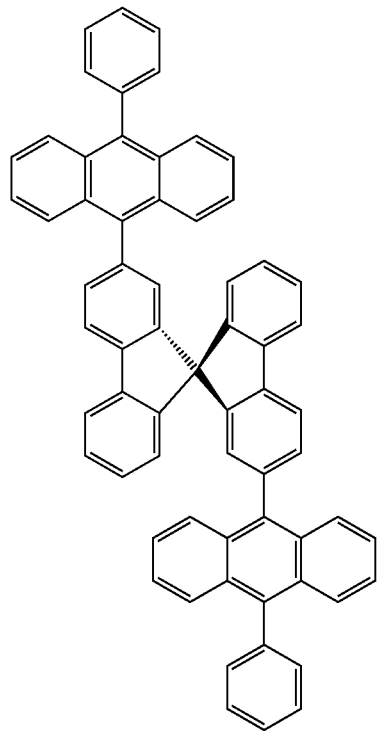
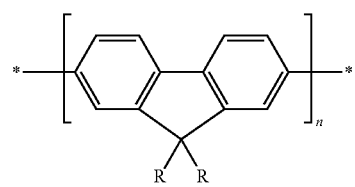
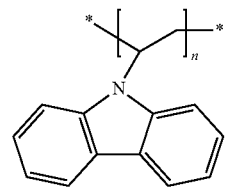
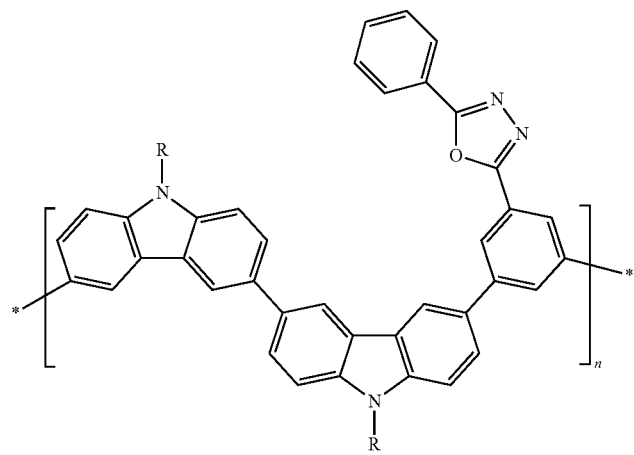
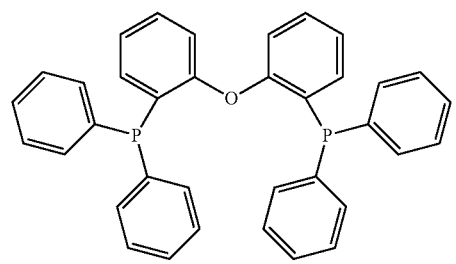
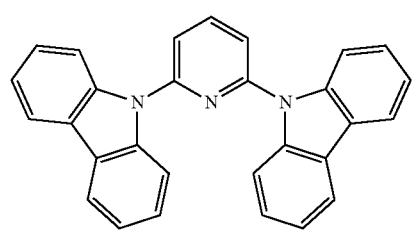
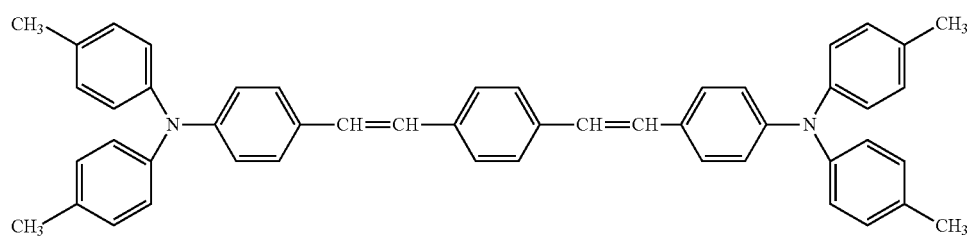

Preferred examples of a compound that may be used as the hole injection material are shown below.
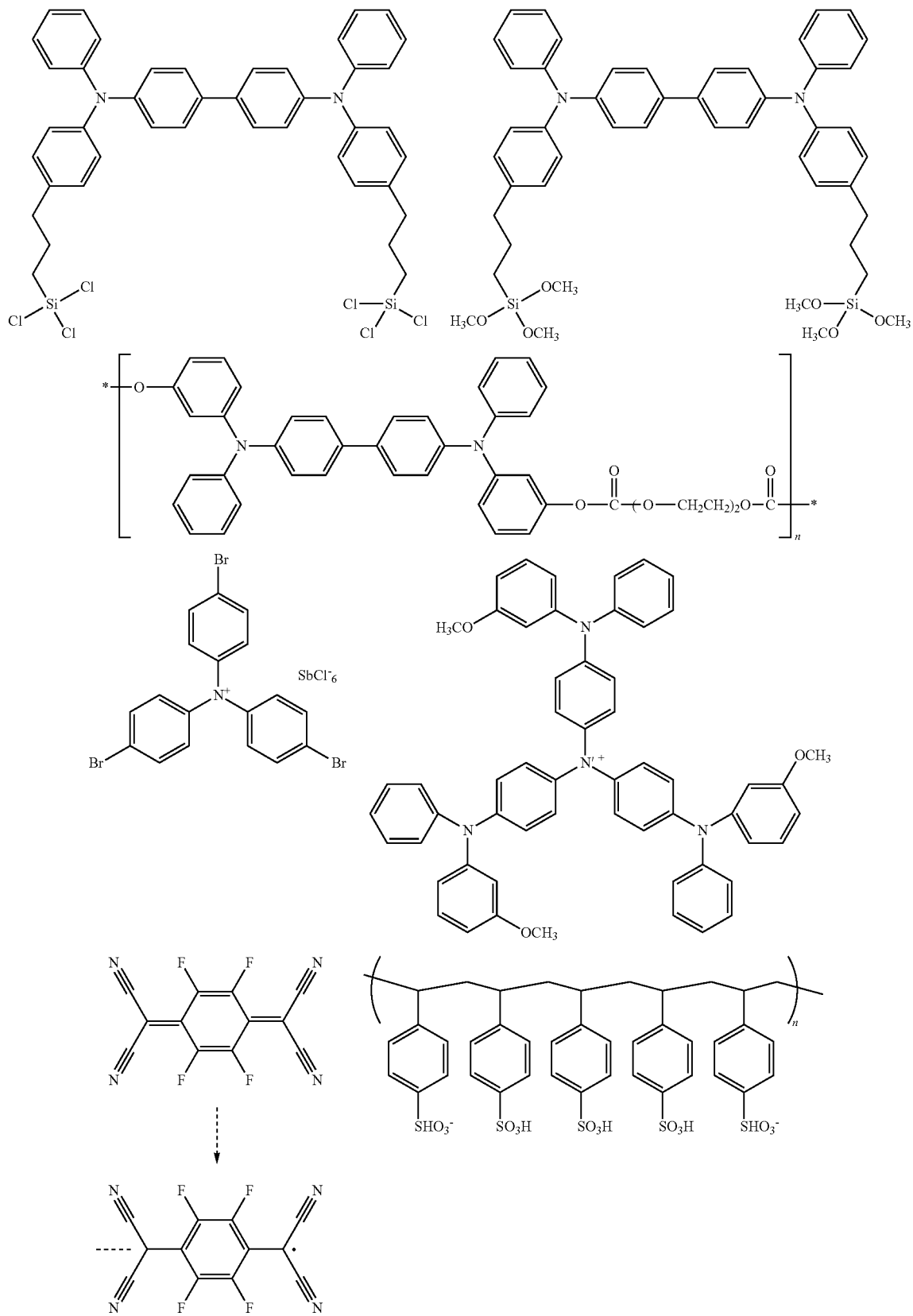

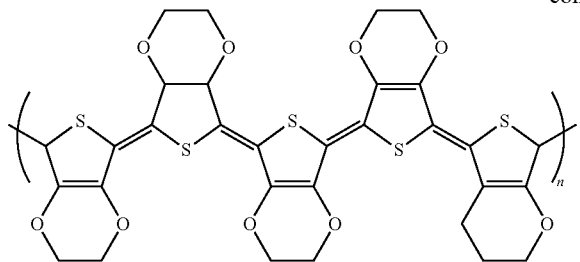
Preferred examples of a compound that may be used as the hole transporting material are shown below.
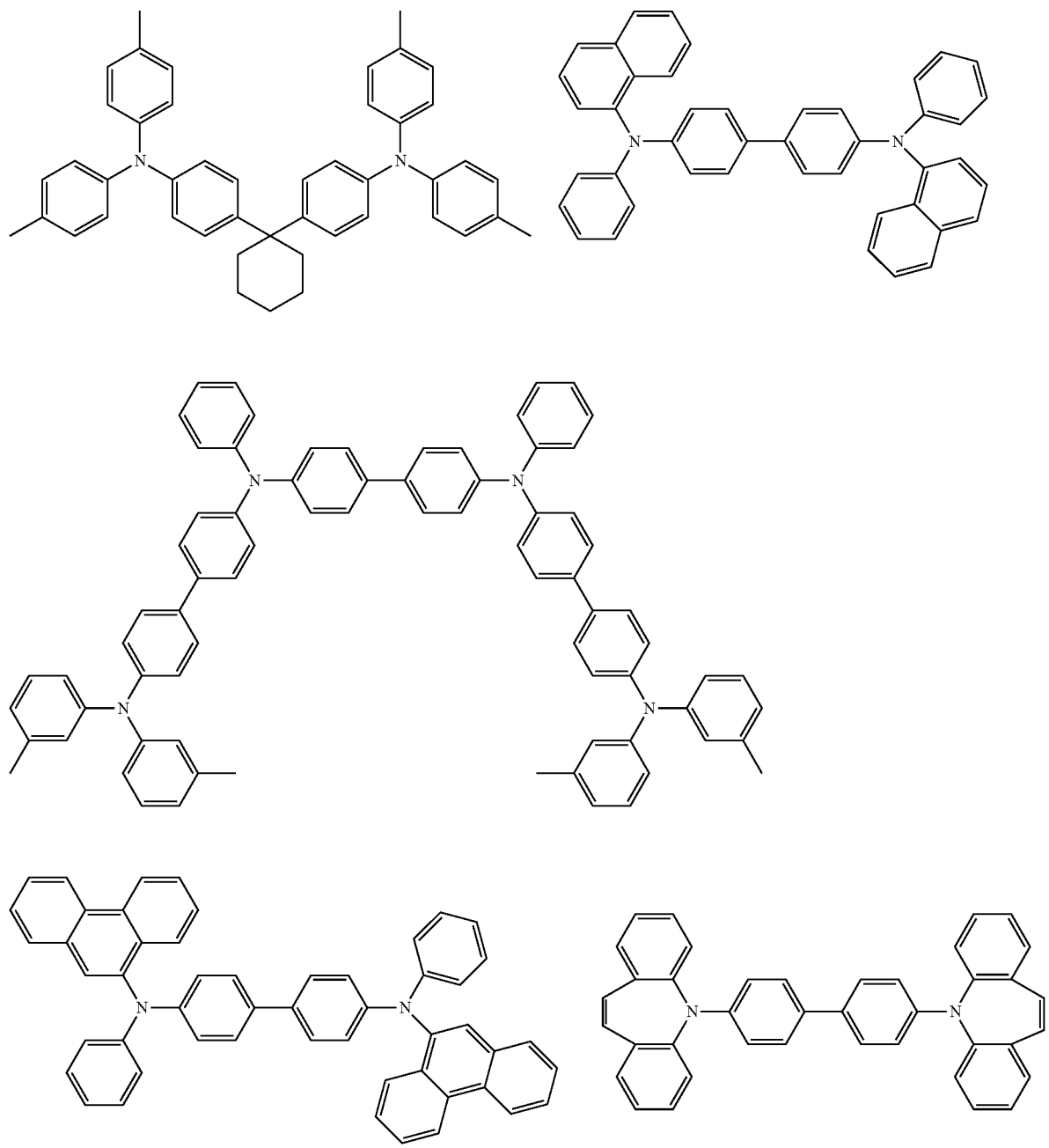

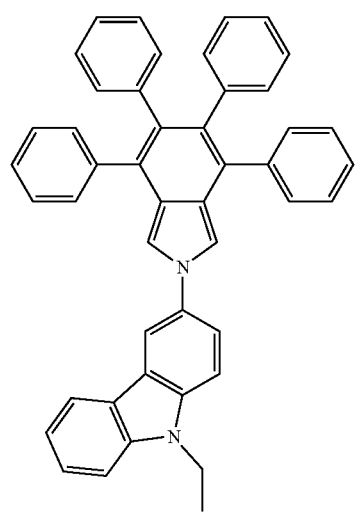
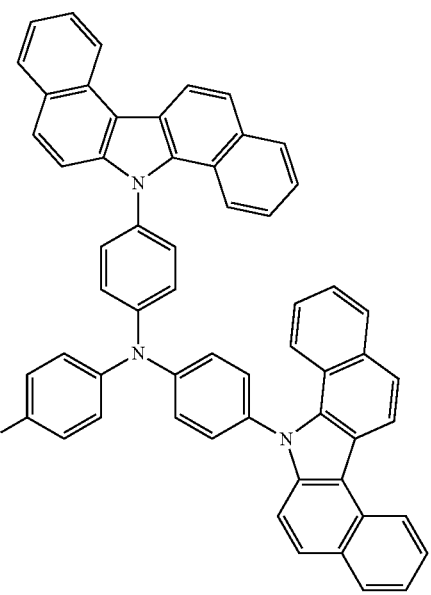
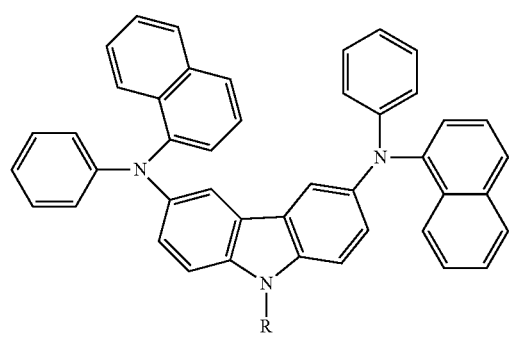
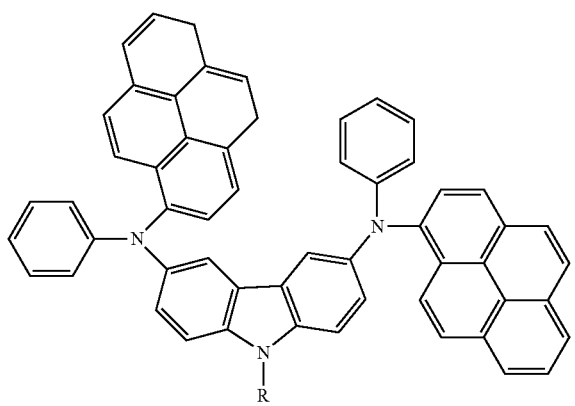
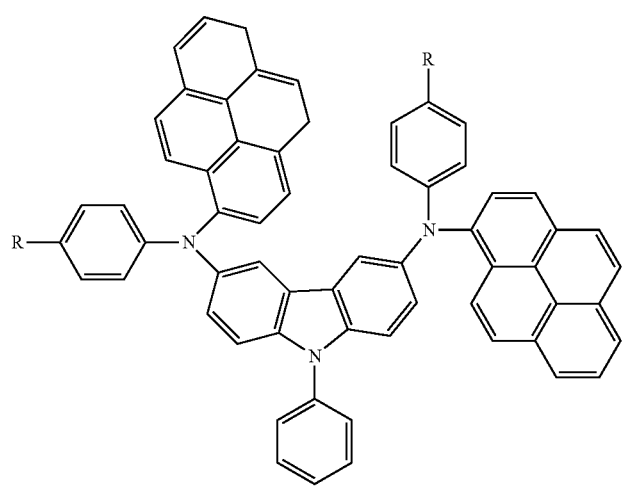

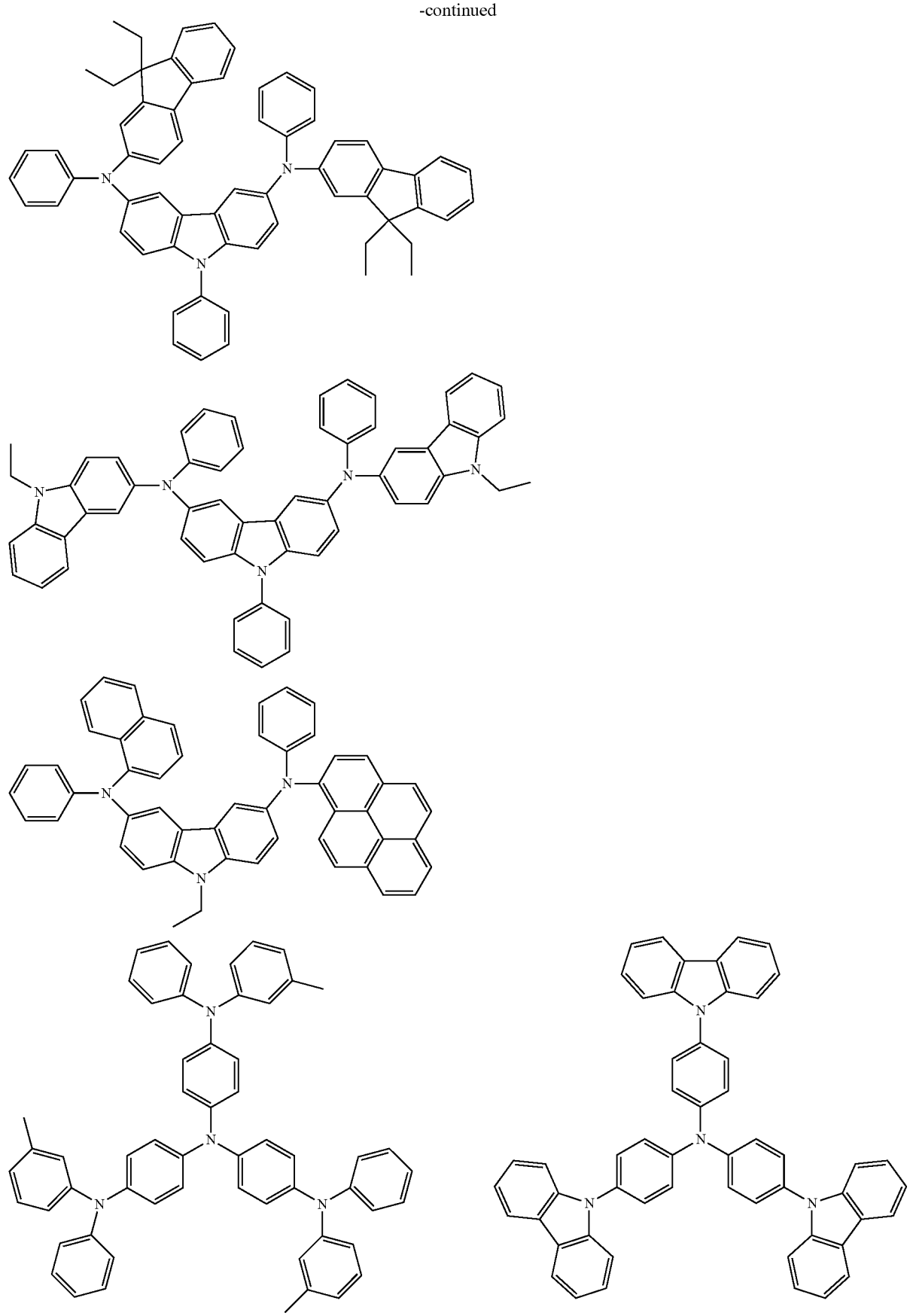

33
34
-continued
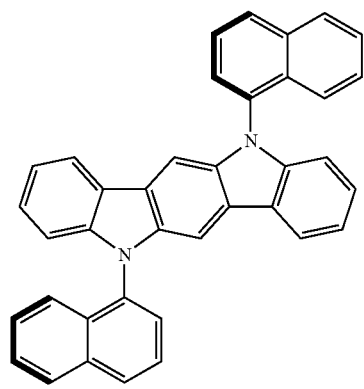
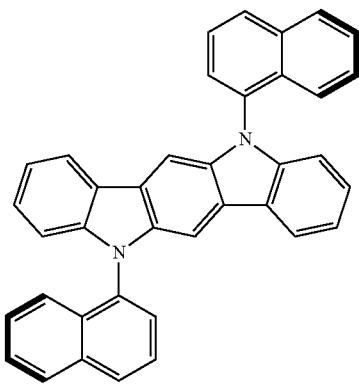
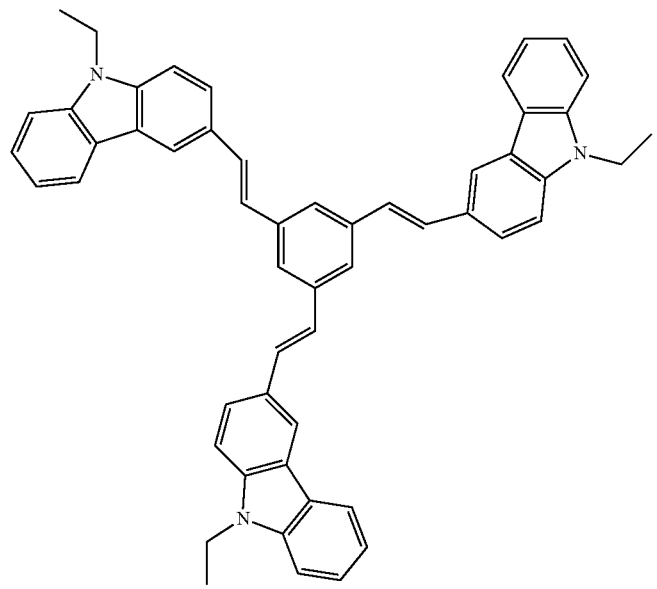
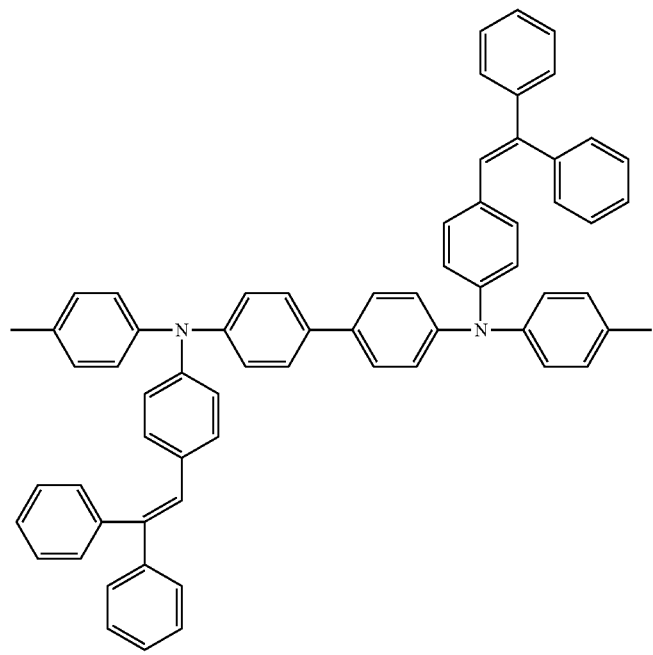

-continued
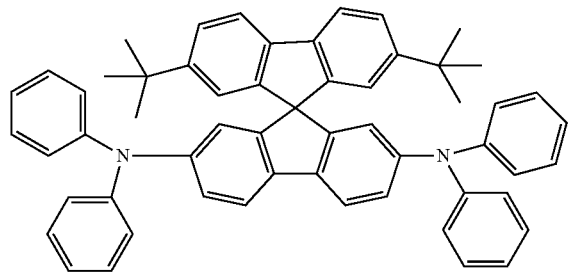
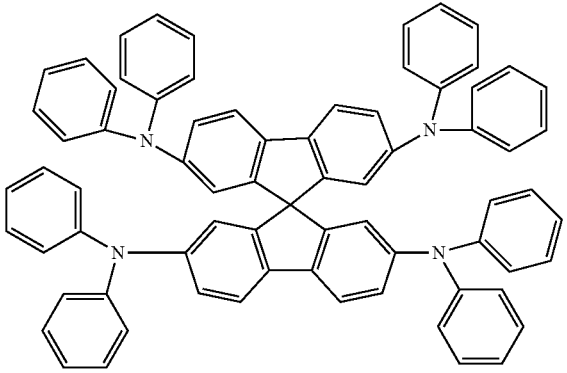
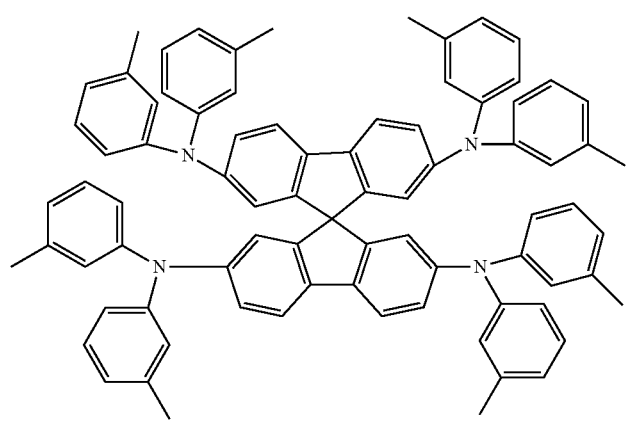
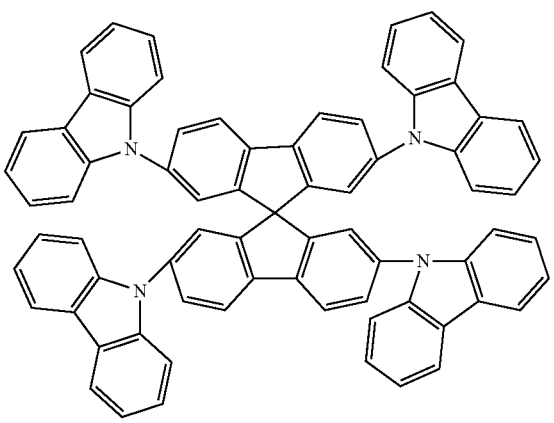
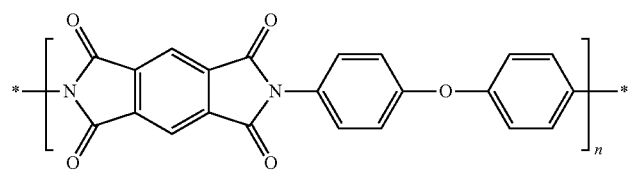
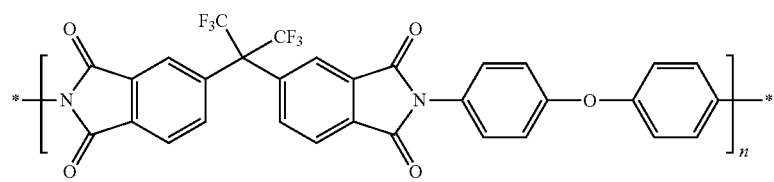
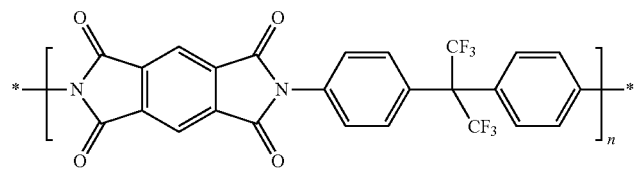
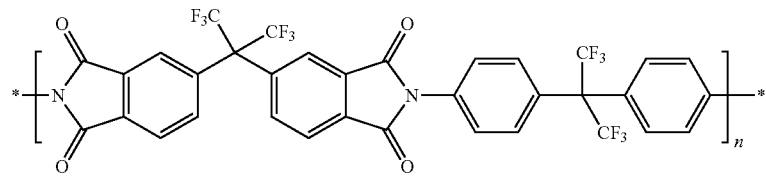

-continued
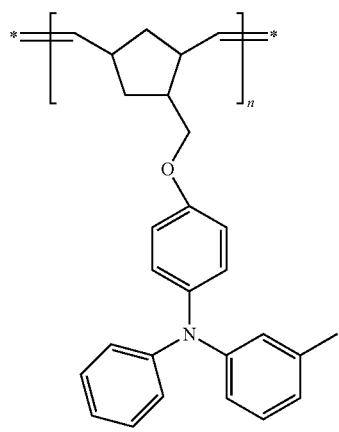
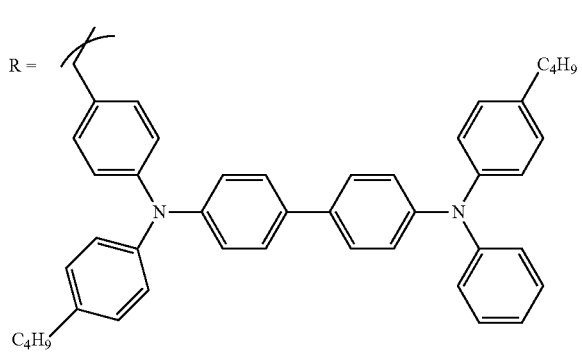
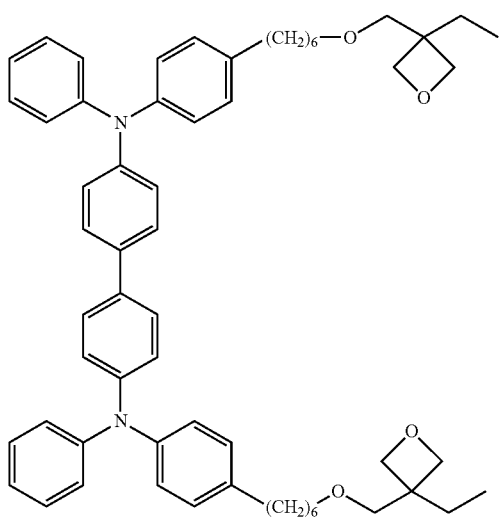
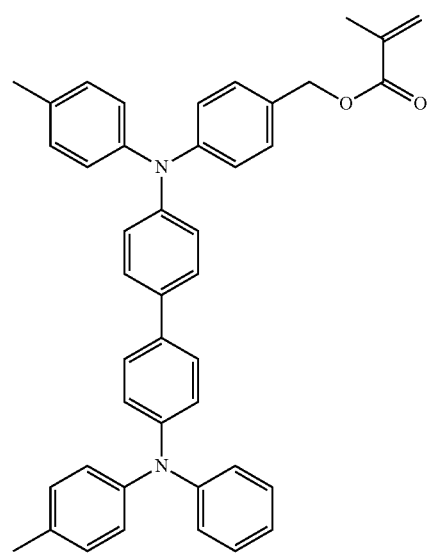
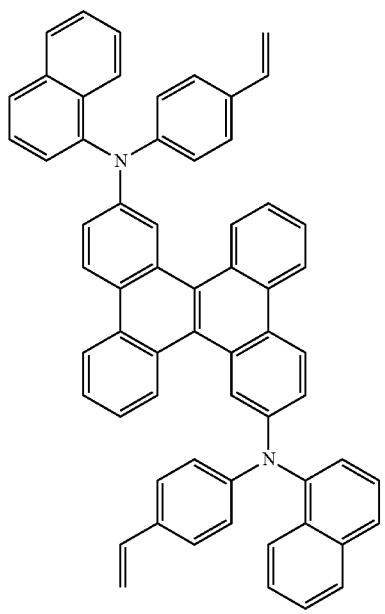
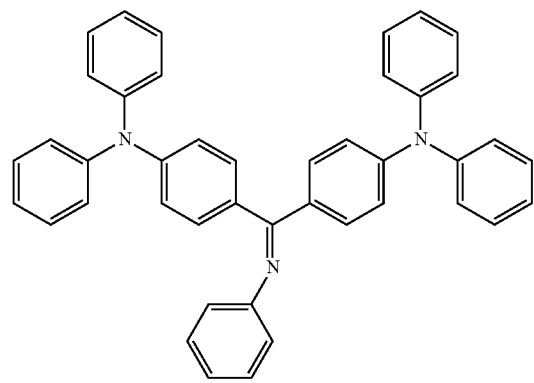

-continued
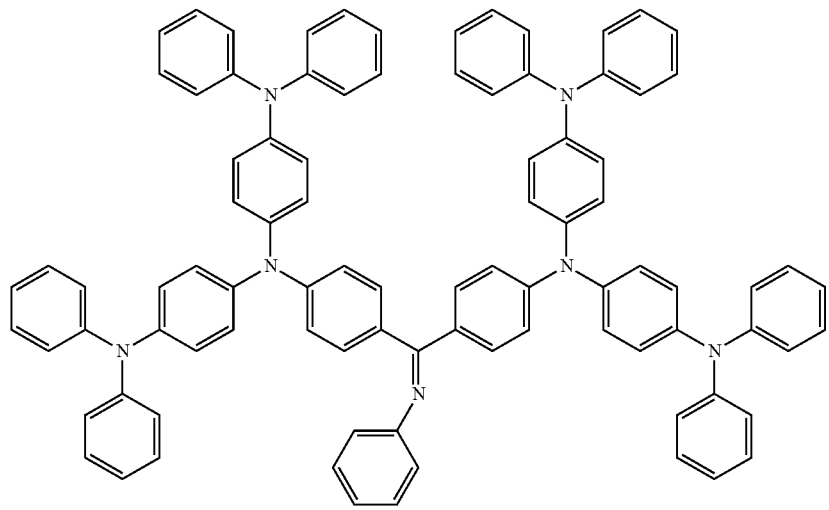
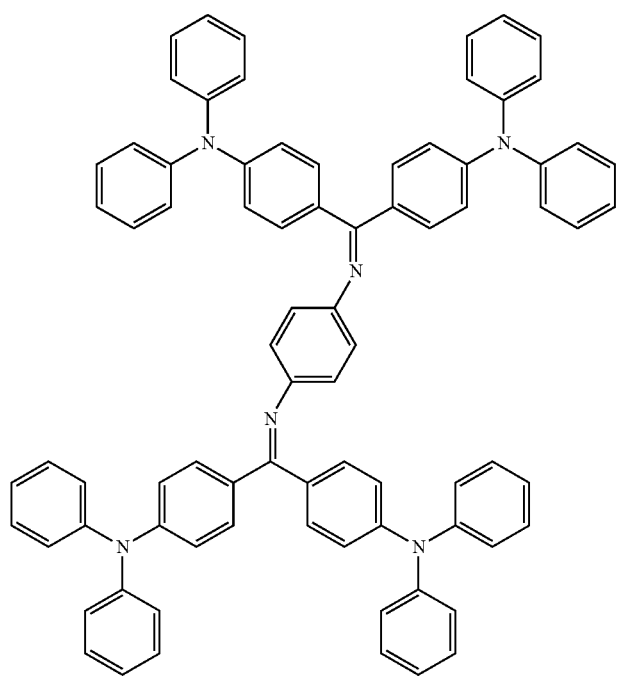

-continued
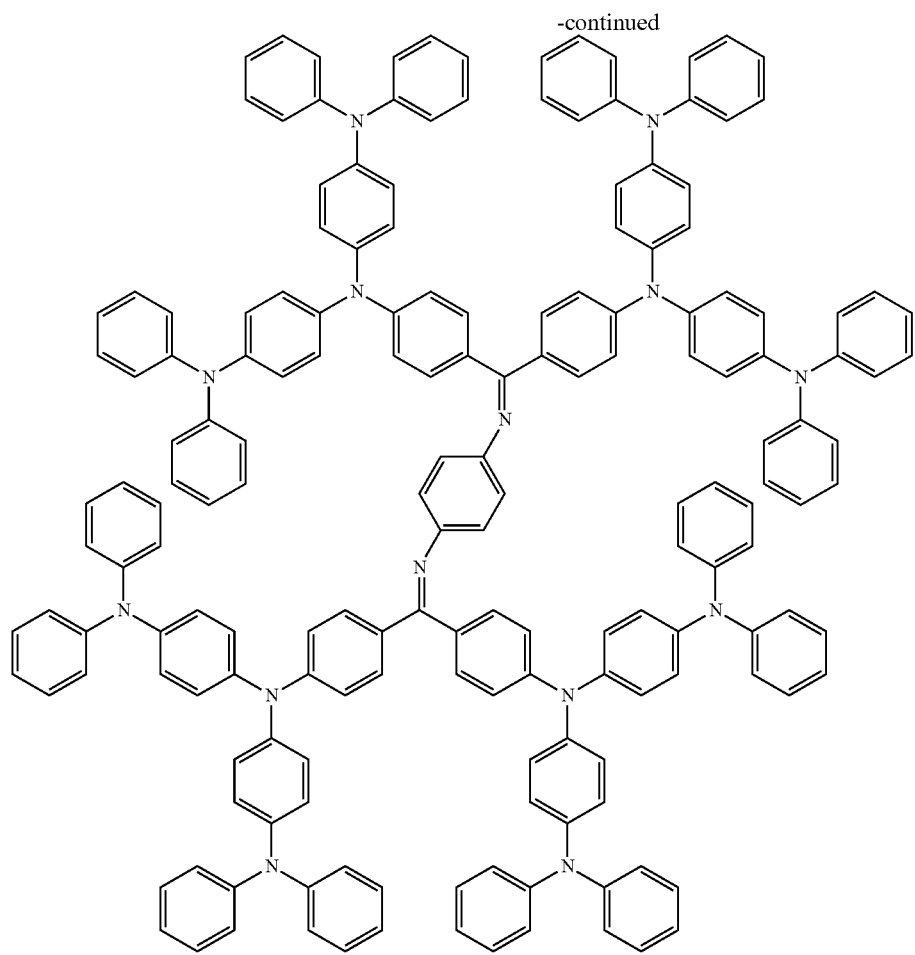
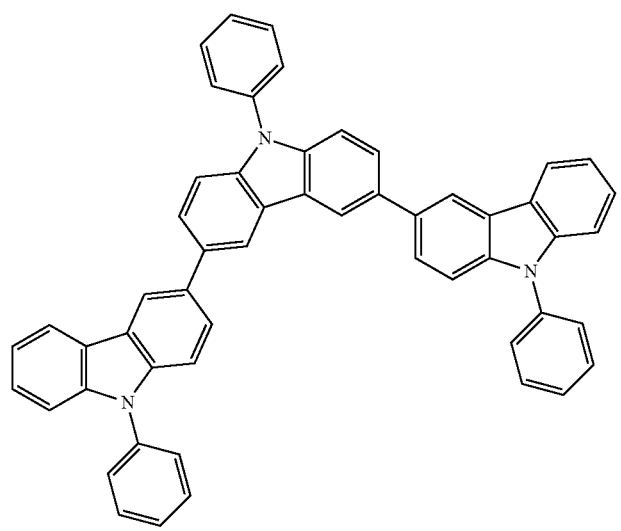

Preferred examples of a compound that may be used as the electron barrier material are shown below.
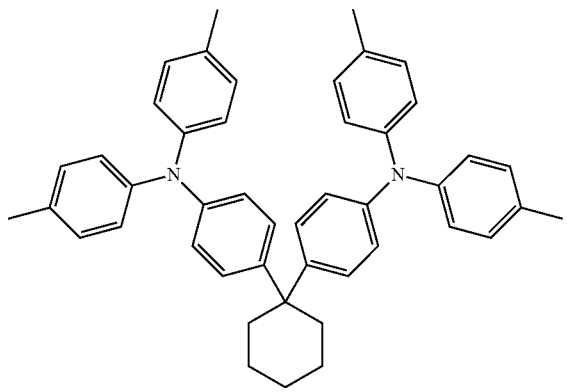
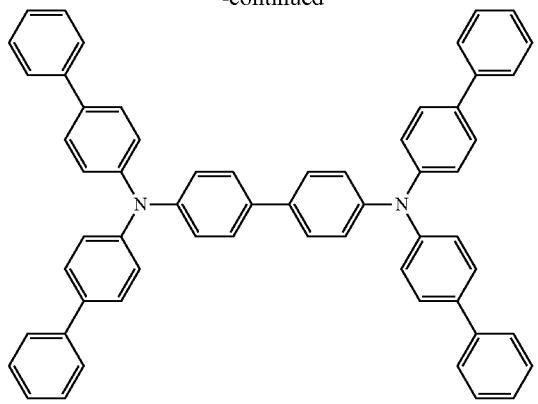
Preferred examples of a compound that may be used as the hole barrier material are shown below.
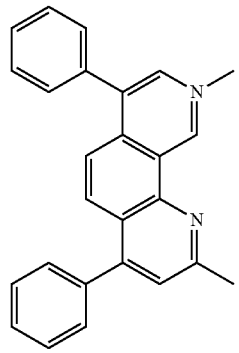
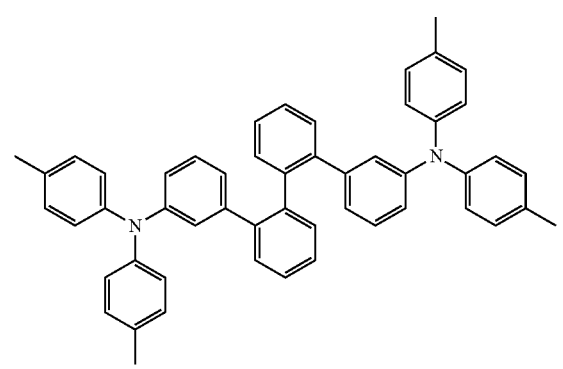
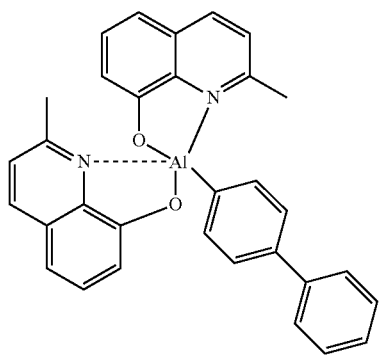
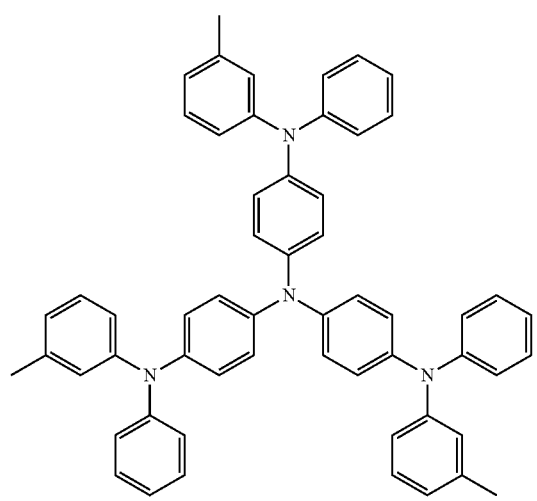
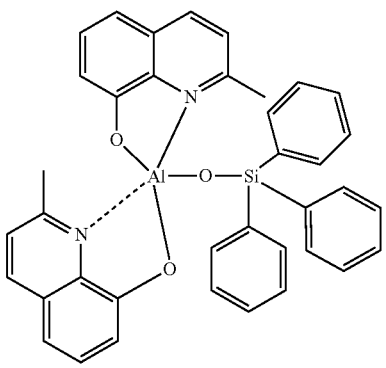

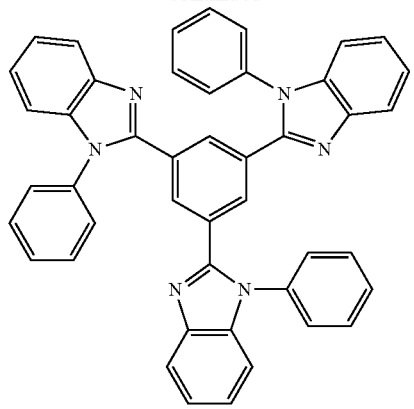
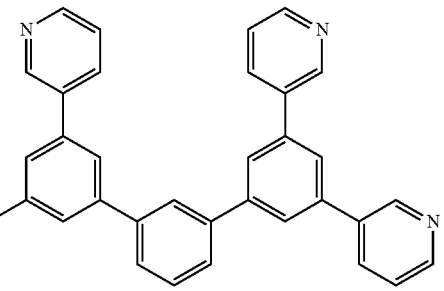
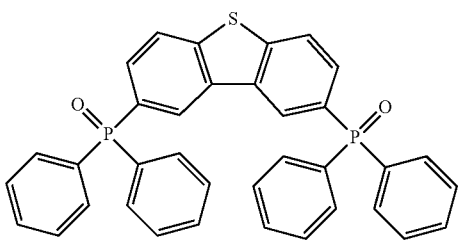
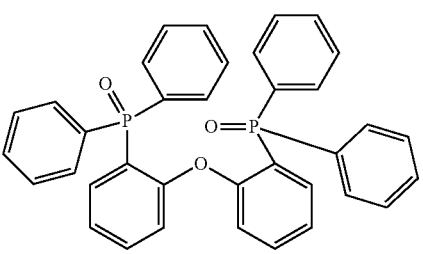
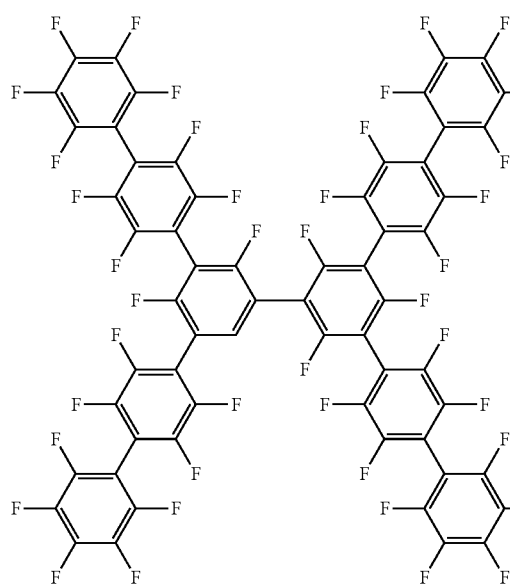
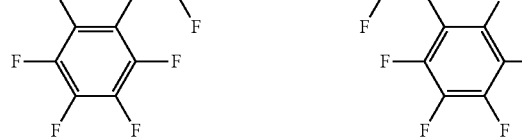
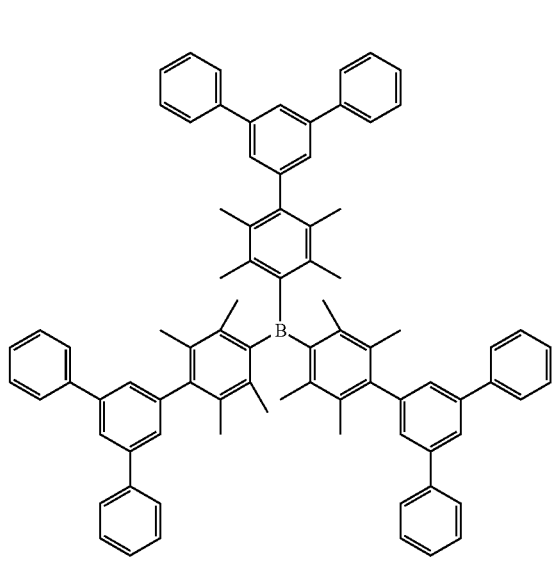
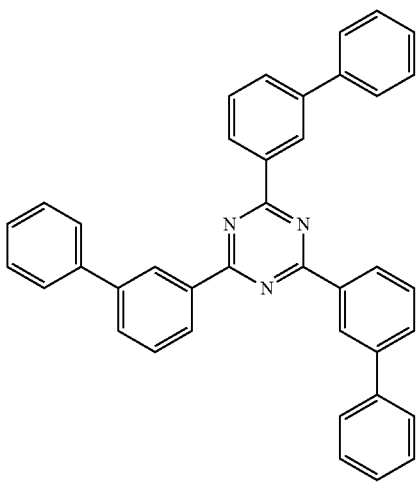
Preferred examples of a compound that may be used as the electron transporting material are shown below.

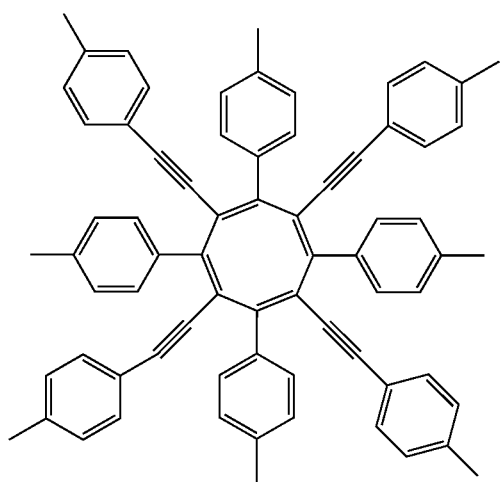
47
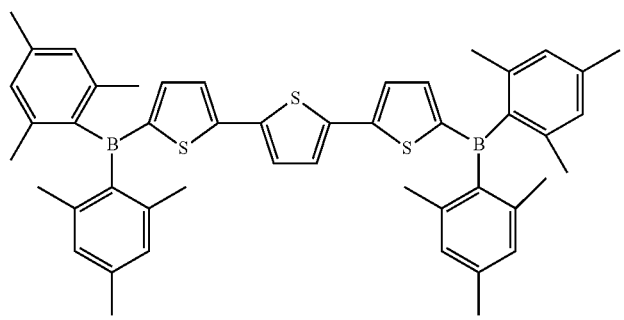
48
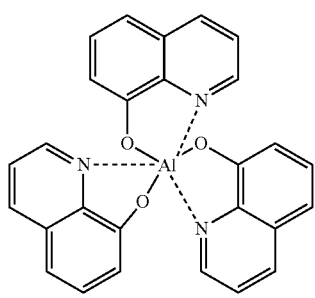
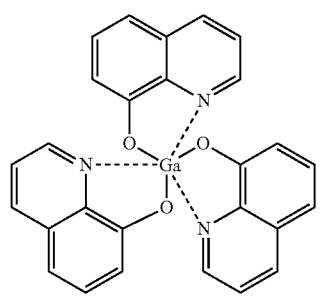
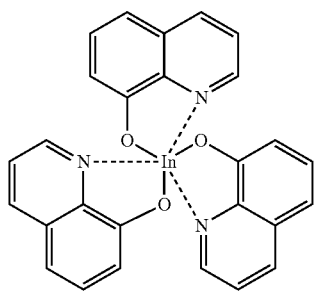
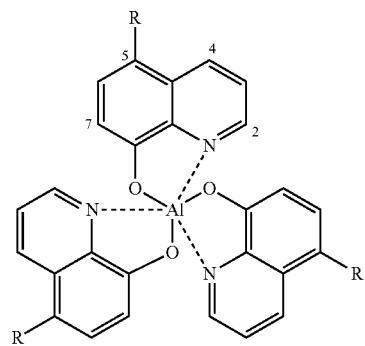
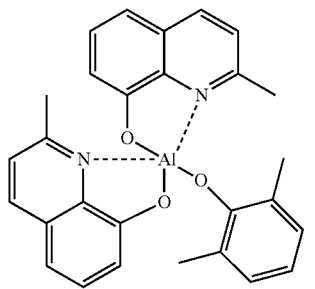
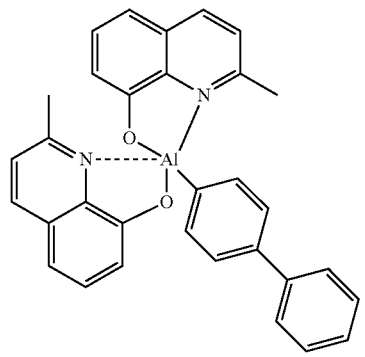

-continued
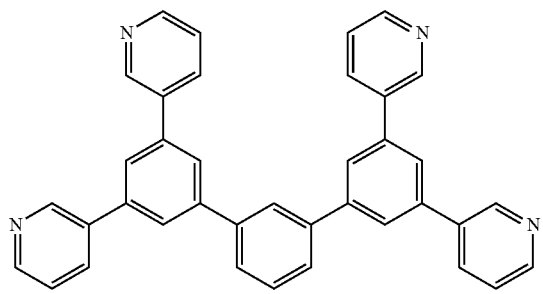
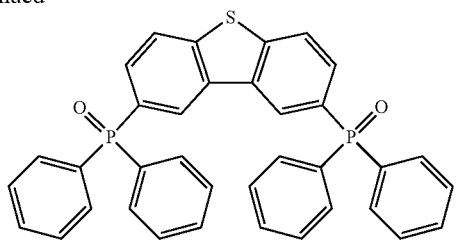
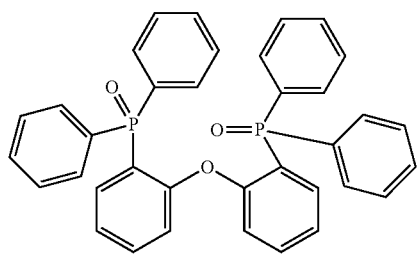
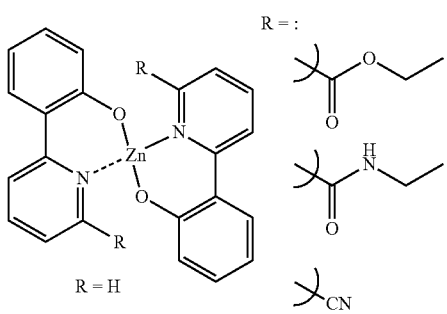
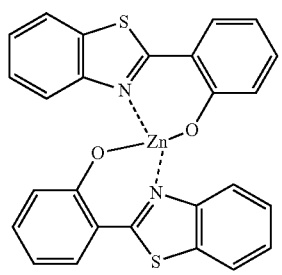
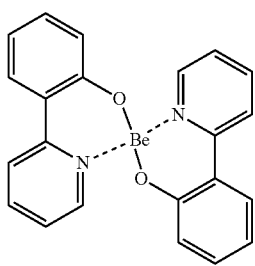
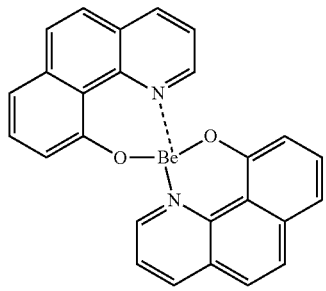
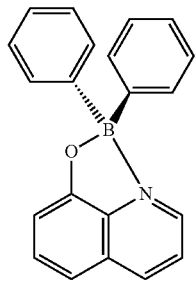

-continued
51
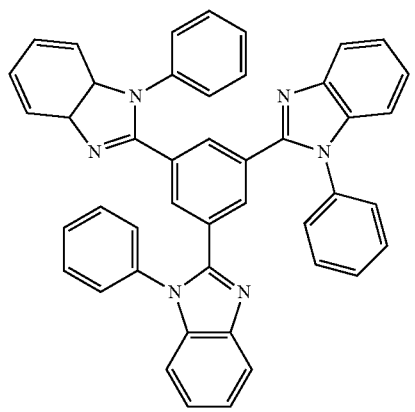
52
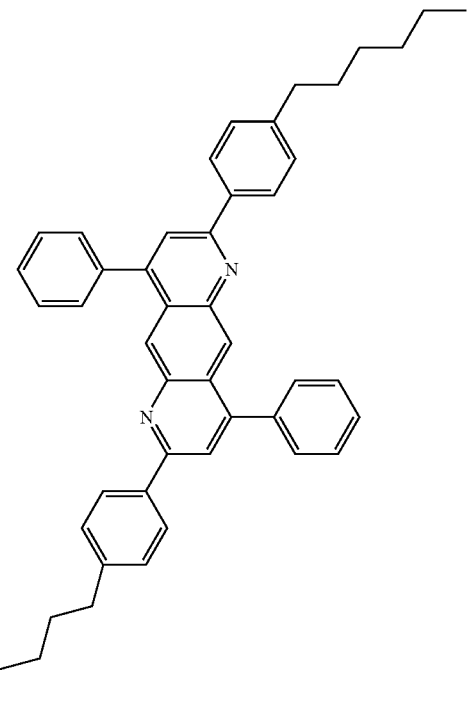
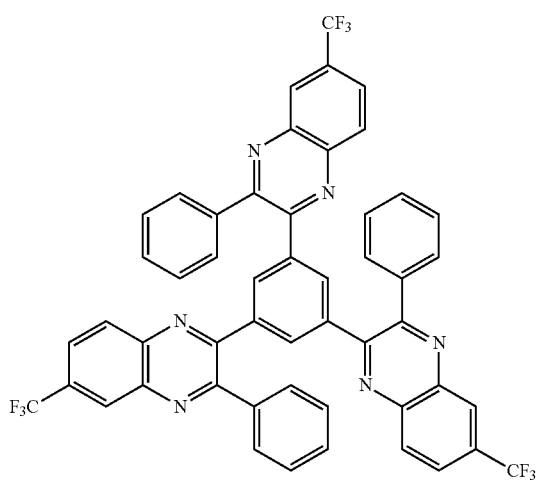
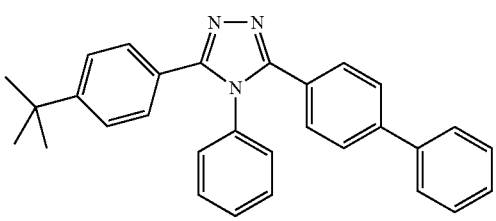
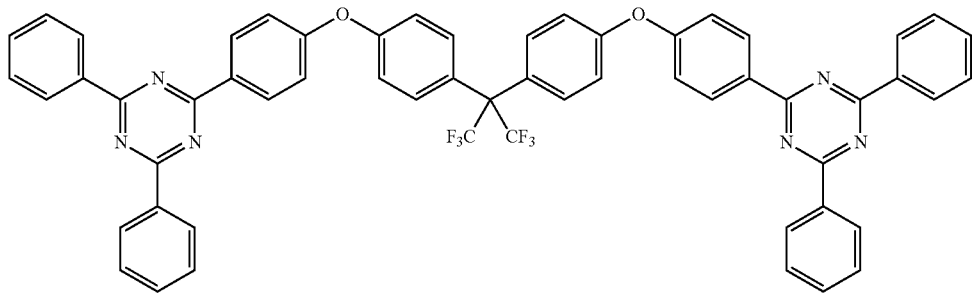
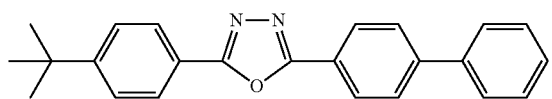

-continued
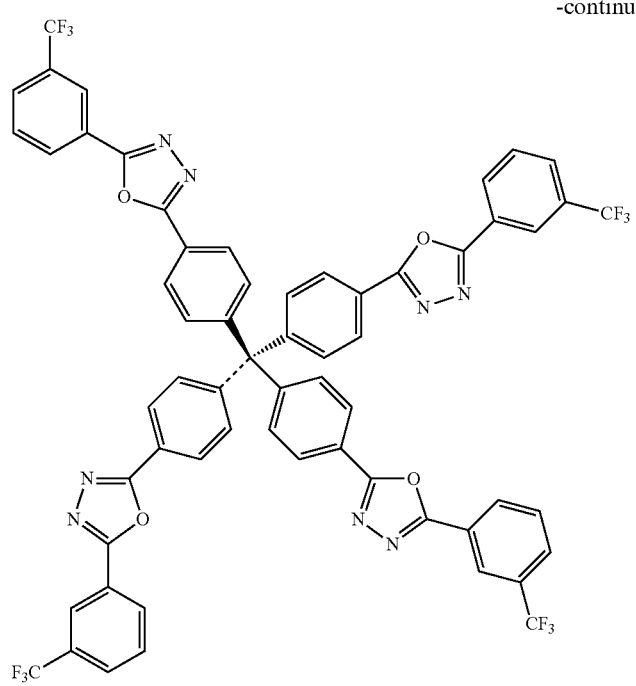
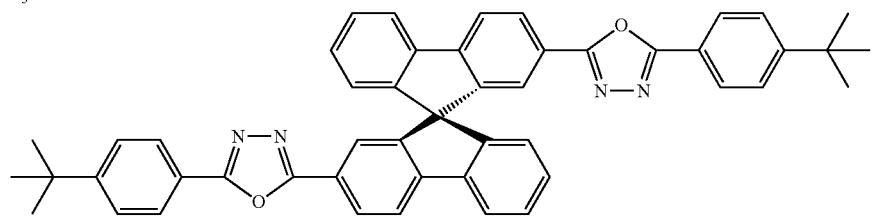
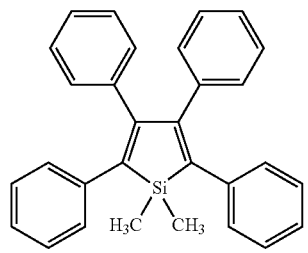
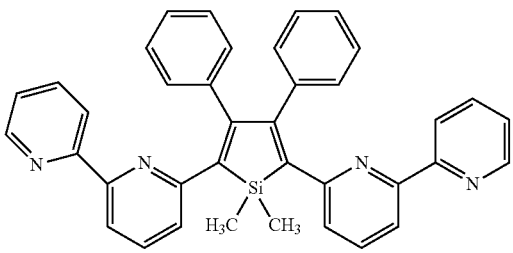
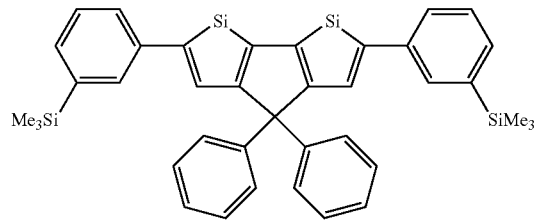
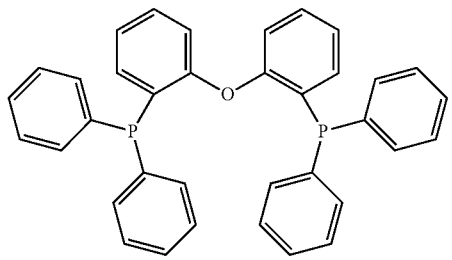
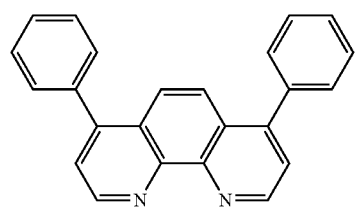
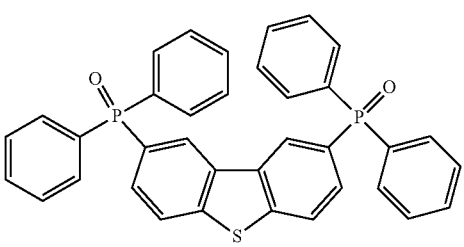

Preferred examples of a compound that may be used as the electron injection material are shown below.

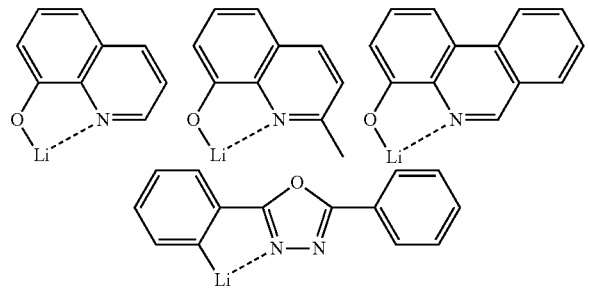

Preferred examples of a compound as a material that may be added are shown below. For example, the compound may be added as a stabilizing material.

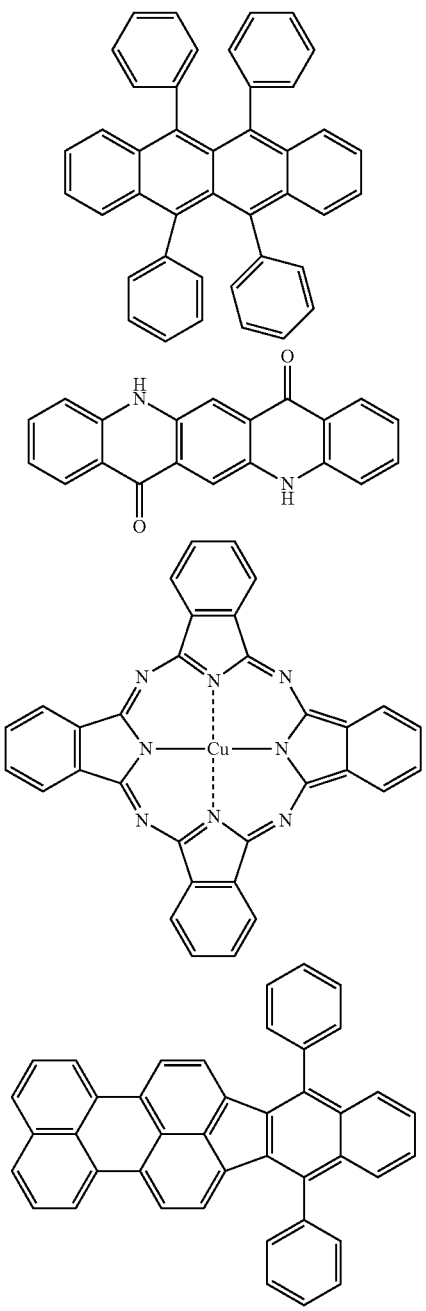

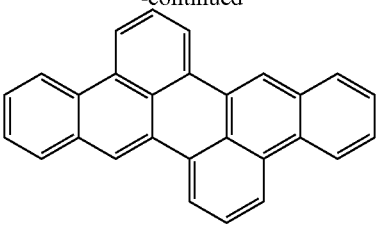

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter fluorescence lifetime than the delayed fluorescent light, and thus the light emission lifetime may be distinguished between the fluorescent light and the delayed fluorescent light.

The phosphorescent light may substantially not observed with a normal organic compound at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the nπ* type compound in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to examples below. The materials, processes, procedures and the like shown below may be appropriately modified unless they deviate from the substance of the invention. Accordingly, the scope of the invention is not construed as being limited to the specific examples shown below. The light emission characteristics were evaluated by using UV-VIS Spectrophotometer (UV-2550, produced by Shimadzu Corporation), Fluorescent Spectrophotometer (FP-6500, produced by JASCO Corporation), Fluorescence Lifetime Measurement System (C11367-03, produced by Hamamatsu Photonics K.K.), Integrating Sphere Photometer (C9920-02, produced by Hamamatsu Photonics K.K.), Multichannel Photometer (PMA-11, produced by Hamamatsu Photonics K.K.), Semiconductor Parameter Analyzer (E5270, produced by Agilent Technologies, Inc.), Optical Power Meter (1930C, produced by Newport Corporation), and Optical Spectrometer (SD2000, produced by Ocean Optics, Inc.)

(1) Production and Evaluation of Organic Photoluminescent Device Using Compound 1

A toluene solution of the compound 1 (concentration: $10^{-5}$ mol/L) and an acetonitrile solution of the compound 1 (concentration: $10^{-5}$ mol/L) were prepared in a glove box under an Ar atmosphere.

The compound 1 and DPEPO were vapor-deposited from separate vapor deposition sources on a quartz substrate by a vacuum vapor deposition method under a condition of a vacuum degree of $4\times10^{-4}$ Pa or less to provide a thin film having a thickness of 100 nm and a concentration of the compound 1 of 6.0% by weight, which was designated as an organic photoluminescent device.

Figure 2:
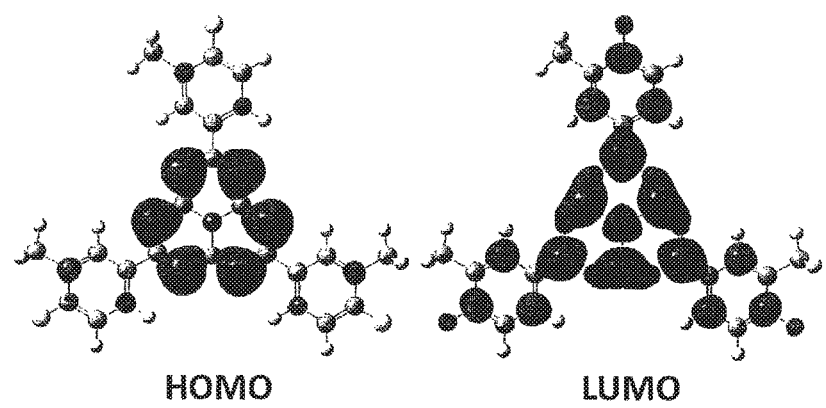
FIG. 2 is an illustration showing the spatial distributions of the HOMO and the LUMO of the compound 1 in Example.
Figure 3:
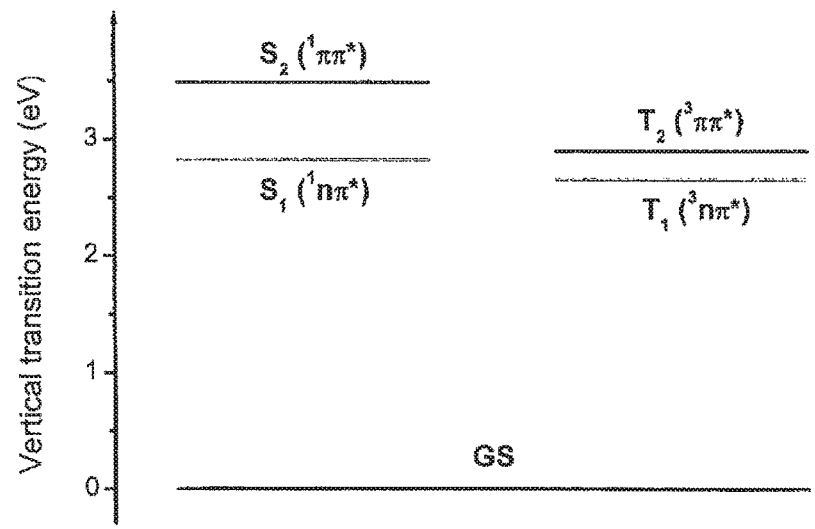
FIG. 3 is a graph showing the excited singlet energy levels $S_1$ and $S_2$ and the excited triplet energy levels $T_1$ and $T_2$ of the compound 1 in Example.
Figure 4:
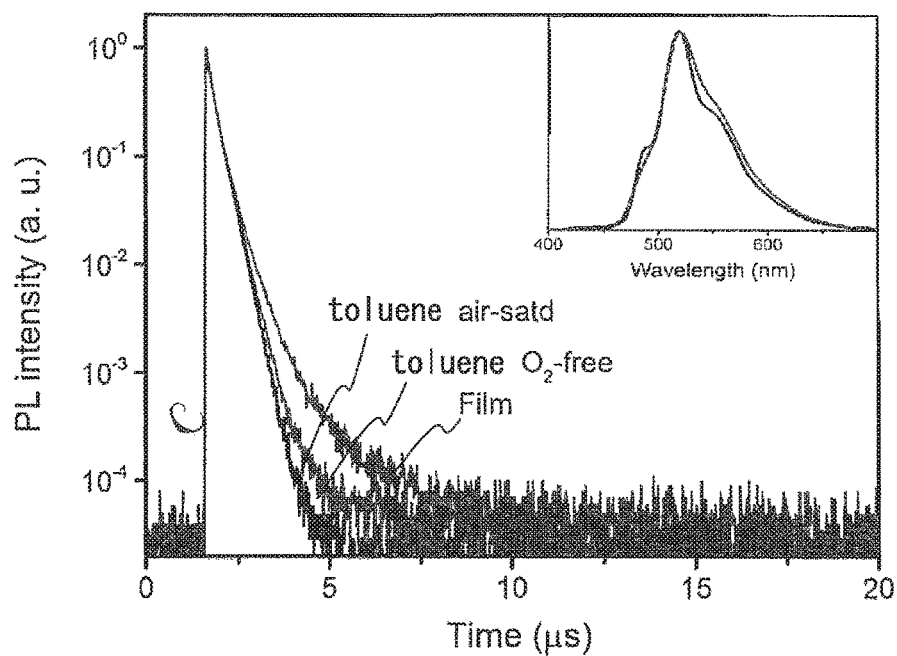
FIG. 4 shows the transient decay curves and the light emission spectra of the toluene solution of the compound 1 and the thin film of the compound 1 and DPEPO in Example.

FIG. 1 shows the results of measurement of the ultraviolet-visible absorption spectra and the light emission spectra with excitation light of 450 nm of the toluene solution and the acetonitrile solution of the compound 1. FIG. 2 shows the spatial distributions of the HOMO and the LUMO of the compound 1 obtained according to DFT (density functional theory) using Gaussian 09 program, and FIG. 3 shows the excited singlet energy levels $S_1$ ($^1n\pi^*$) and $S_2$ ($^1n\pi^*$) and the excited triplet energy levels $T_1$ ($^3n\pi^*$) and $T_2$ ($^3n\pi^*$) of the compound 1. FIG. 4 shows the results of measurement of the transient decay curves of the toluene solution of the compound 1 and the thin film of the compound 1 and DPEPO at room temperature.

As shown in FIG. 1, in the absorption spectrum of the toluene solution of the compound 1, strong absorption with a peak at 327 nm and weak absorption with a peak at 450 nm were confirmed. The strong absorption with a peak at 327 nm is absorption derived from the $n\pi^*$ transition of the π conjugated system, and the weak absorption with a peak at 450 nm is absorption derived from the $n\pi^*$ transition of the lone electron pair and the it non-bonding molecular orbital of the nitrogen atom. In the absorption spectrum of the acetonitrile solution of the compound 1, it was confirmed that the weak absorption band in a wavelength range of from 400 to 500 nm was shifted to the short wavelength side (blue shift) as compared to that in the toluene solution. The blue shift of the absorption band is caused by the stabilization of the lone electron pair of the nitrogen atom with acetonitrile, which has a higher polarity than toluene, and is a characteristic behavior of an absorption peak derived from $n\pi^*$ transition.

The toluene solution of the compound 1 had a photoluminescence quantum efficiency $\Phi_F$ of 0.26, a fluorescence lifetime $\tau_F$ of 252 ns, and a fluorescent radiation constant $k_F$ ($=\Phi_F/\tau_F$) obtained therefrom of $1.0\times10^{-6}$ $s^{-1}$. These low fluorescent radiation constant and absorption constant are characteristic properties found in a molecule that undergoes $n\pi^*$ transition.

It was confirmed from the above that the compound 1 was a light-emitting material that underwent $n\pi^*$ transition.

As shown by the spatial distributions of the electron orbitals in FIG. 2, in the ground state, the HOMO overlaps mainly with the nitrogen atom having an $sp^2$ hybrid orbital of the heptazine nucleus, and the LUMO is distributed over the entire π conjugated system.

FIG. 3 shows the results of calculation of the energy levels based on the spatial distributions of the electron orbitals. In the $S_1$ transition (HOMO→LUMO) the oscillator strength (f) was 0.0002, and the perpendicular transition energy was 2.8256 eV (439 nm), and in the $S_2$ transition (HOMO-1→LUMO), the oscillator strength (f) was 0.4590, and the perpendicular transition energy was 3.4924 eV (355 nm). The difference in energy between the energy level $S_1$ ($^1n\pi^*$) and energy level $T_1$ ($^3n\pi^*$) was 0.165 eV, which was a considerably small value. The difference in energy between the singlet state and the triplet state of the $n\pi^*$ transition was considerably larger than the difference in energy between the singlet state and the triplet state of the $n\pi^*$ transition, but the difference in energy between the energy level $T_2$ ($^3n\pi^*$) and the energy level $T_1$ ($^3n\pi^*$) was 0.24 eV.

It was found from the transient decay curves in FIG. 4 that the toluene solution of the compound 1 had a light emission lifetime of 252 ns in the presence of the air, and the light emission intensity in the long lifetime region was increased under an oxygen-free environment. The increase of the light emission intensity under an oxygen-free environment is derived from the emission of delayed fluorescent light, and it is confirmed from the phenomenon that the compound 1 emits delayed fluorescent light. The thin film of the compound 1 and DPEPO resulted in a higher light emission intensity in the long lifetime region than the toluene solution of the compound 1.

(2) Production and Evaluation of Organic Electroluminescent Device Using Compound 1

Figure 5:
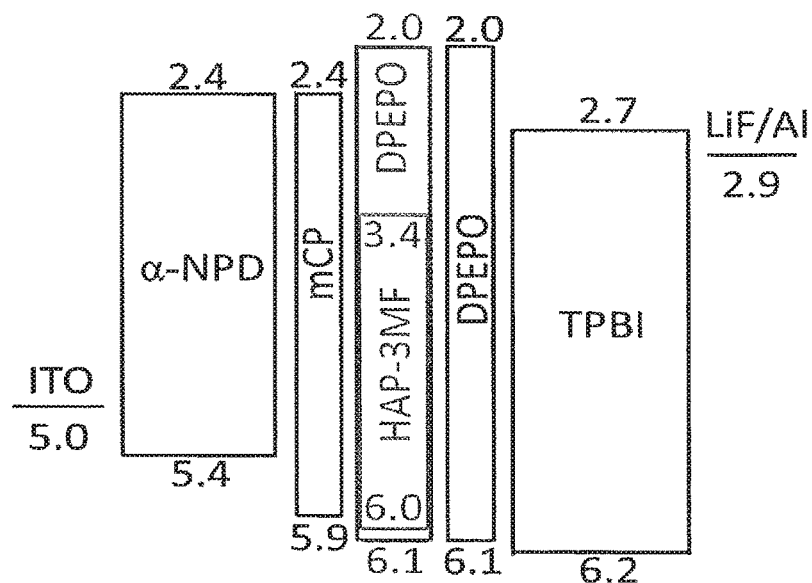
FIG. 5 is a schematic illustration showing the layer structure and the energy diagram of the organic electroluminescent device using the compound 1 in Example.

Thin films were laminated on a glass substrate having formed thereon an anode formed of indium tin oxide (ITO) having a thickness of 100 nm, by a vacuum vapor deposition method at a vacuum degree of $4.0\times10^{-4}$ Pa or less, thereby producing an organic electroluminescent device shown in FIG. 5. Firstly, α-NPD was formed to a thickness of 35 nm on ITO to form a hole transporting layer, and then mCP was formed to a thickness of 10 nm thereon to form an electron barrier layer. Subsequently, the compound 1 and DPEPO were co-deposited thereon from separate vapor deposition sources to form a layer having a thickness of 15 nm, which was designated as a light-emitting layer. At this time, the concentration of the compound 1 was 6.0% by weight. DPEPO was then formed to a thickness of 10 nm to form a hole barrier layer, and TPBI was formed thereon to a thickness of 40 nm to form an electron transporting layer. Furthermore, lithium fluoride (LiF) was vacuum vapor-deposited to a thickness of 0.8 nm, and then aluminum (Al) was vapor-deposited to a thickness of 100 nm to form a cathode, thereby completing an organic electroluminescent device.

Figure 6:
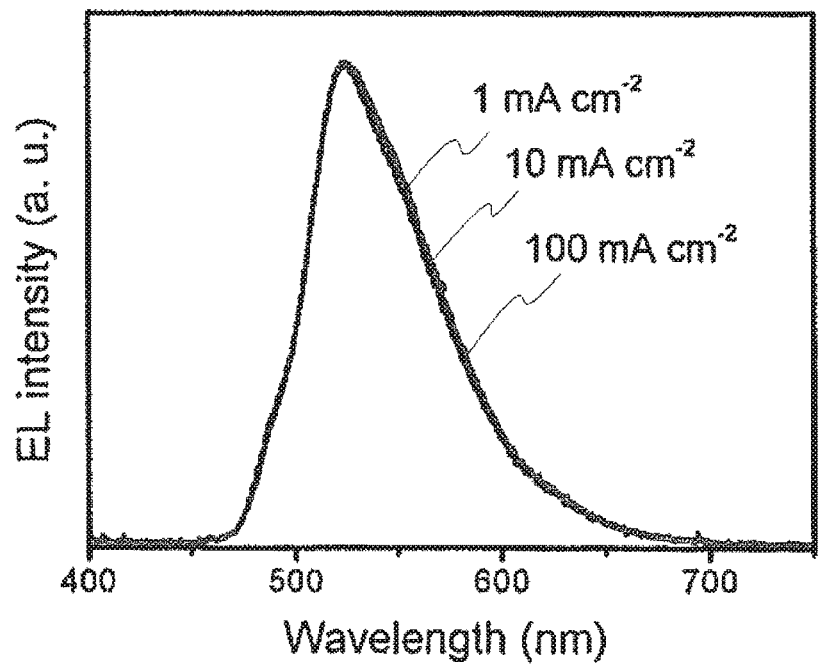
FIG. 6 shows the light emission spectra of the organic electroluminescent device using the compound 1 in Example.
Figure 7:
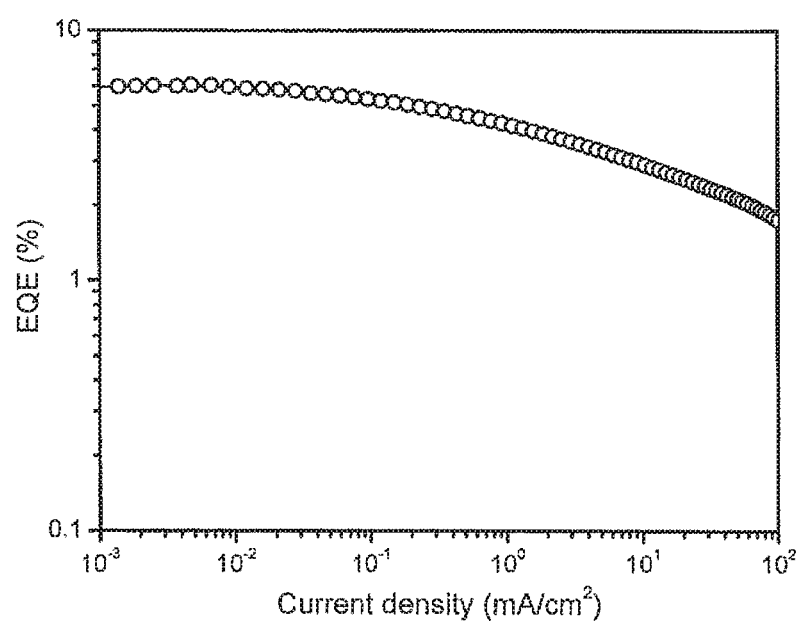
FIG. 7 is a graph showing the current density-external quantum efficiency characteristics of the organic electroluminescent device using the compound 1 in Example.

FIG. 6 shows the results of measurement of the light emission spectra of the organic electroluminescent device thus produced, at current densities of 1 mA/cm², 10 mA/cm², and 100 mA/cm², and FIG. 7 shows the current density-external quantum efficiency characteristics thereof. The organic electroluminescent device using the compound 1 as a light-emitting material achieved a high external quantum efficiency of 6.0%. This value largely exceeds the theoretical limit value (1.3 to 2.0%) of the external quantum efficiency in the case using a normal fluorescent material exhibiting no delayed fluorescence as a light-emitting material.

Compound 1

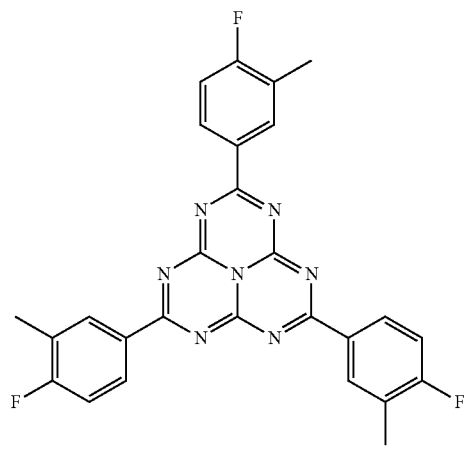

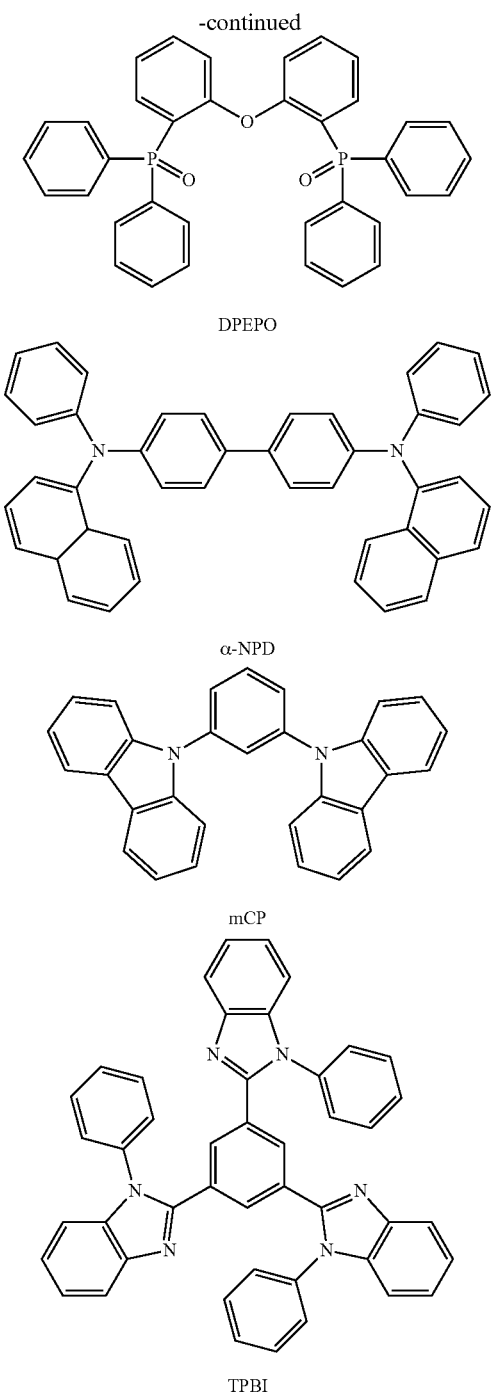

DPEPO

α-NPD mCP

TPBI

The invention claimed is:

1. An organic light-emitting device comprising a light-emitting layer comprising a host material and a compound having a lone electron pair and a π electron orbital,
the compound emitting fluorescent light by such a mechanism that when at least a part of electrons constituting the lone electron pair is excited to an excited triplet state $^3n\pi^*$ through $n\pi^*$ transition, the part of electrons undergoes inverse intersystem crossing from the excited triplet state $^3n\pi^*$ to an excited singlet state $^1n\pi^*$, and returns from the excited singlet state $^1n\pi^*$ to the ground state, at which the fluorescent light is emitted.

2. The organic light-emitting device according to claim 1, wherein the compound has an energy level of the excited triplet state $^3n\pi^*$ through $n\pi^*$ transition that is lower than an energy level of an excited triplet state $^3\pi\pi^*$ through $\pi\pi^*$ transition.

3. The organic light-emitting device according to claim 1, wherein the compound has a difference in energy between the excited triplet state $^3n\pi^*$ and the excited singlet state $^1n\pi^*$ that is smaller than a difference in energy between the excited triplet state $^3n\pi^*$ and the ground state.

4. The organic light-emitting device according to claim 1, wherein the compound contains a nitrogen atom.

5. The organic light-emitting device according to claim 4, wherein the compound has a heteroaromatic ring containing a nitrogen atom.

6. The organic light-emitting device according to claim 5, wherein the compound is a derivative of heptazine.

7. The organic light-emitting device according to claim 6, wherein the compound is a compound represented by the following general formula (1):

General Formula (1)

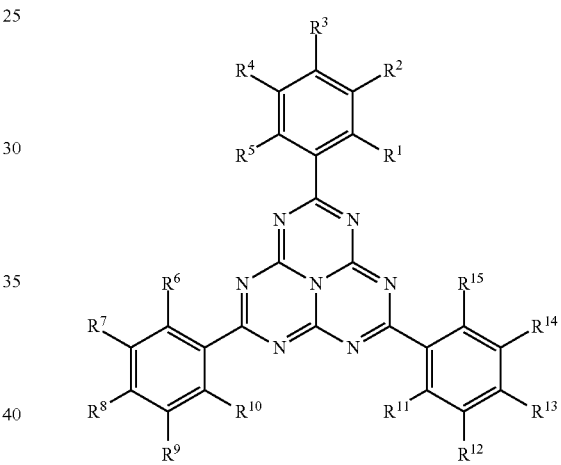

wherein in the general formula (1), $R^1$ to $R^{15}$ each independently represent a hydrogen atom or a substituent, provided that at least one of $R^1$ to $R^5$, at least one of $R^6$ to $R^{10}$, and at least one of $R^{11}$ to $R^{15}$ each independently represent a halogen atom, at least one of the balance of $R^1$ to $R^5$, at least one of the balance of $R^6$ to $R^{10}$, and at least one of the balance of $R^{11}$ to $R^{15}$ each independently represent an alkyl group, and $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

8. The organic light-emitting device according to claim 1, wherein the light-emitting device comprises a pair of electrodes, and an organic layer including a light-emitting layer provided between the pair of electrodes, and the compound is contained at least in the light-emitting layer.

9. The organic light-emitting device according claim 8, wherein the light-emitting layer contains a light-emitting dopant, an assist dopant, and a host, and the compound is used as the assist dopant.

10. An organic light-emitting device comprising a light-emitting layer comprising a host material and a compound represented by the following general formula (1):

General Formula (1)

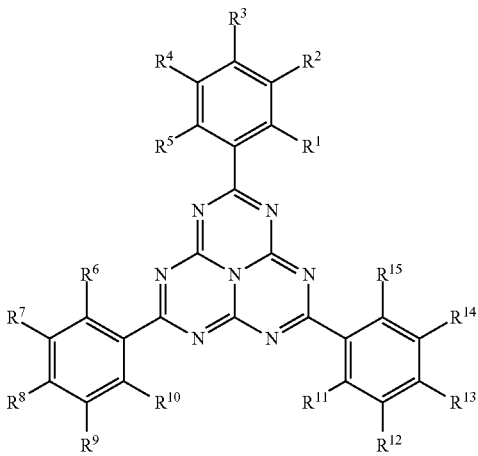

wherein in the general formula (1), $R^1$ to $R^{15}$ each independently represent a hydrogen atom or a substituent, provided that at least one of $R^1$ to $R^5$, at least one of $R^6$ to $R^{10}$, and at least one of $R^{11}$ to $R^{15}$ each independently represent a halogen atom, at least one of the balance of $R^1$ to $R^5$, at least one of the balance of $R^6$ to $R^{10}$, and at least one of the balance of $R^{11}$ to $R^{15}$ each independently represent an alkyl group, and $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

11. The organic light-emitting device according to claim 10, wherein in the general formula (1), any one of $R^1$ to $R^5$, any one of $R^6$ to $R^{10}$, and any one of $R^{11}$ to $R^{15}$ each independently represent a halogen atom, and any one of the balance of $R^1$ to $R^5$, any one of the balance of $R^6$ to $R^{10}$, and any one of the balance of $R^{11}$ to $R^{15}$ each independently represent an alkyl group.

12. The organic light-emitting device according to claim 10, wherein the substitution position of the alkyl group on the benzene ring is an o-position with respect to the substitution position of the halogen atom.

13. The organic light-emitting device according to claim 10, wherein in the general formula (1), $R^3$, $R^8$, and $R^{13}$ each independently represent a halogen atom.

14. The organic light-emitting device according to claim 13, wherein in the general formula (1), $R^2$, $R^7$, and $R^{12}$ each independently represent an alkyl group.

15. The organic light-emitting device according to claim 10, wherein the halogen atom is a fluorine atom.

16. The organic light-emitting device according to claim 10, wherein the alkyl group is a methyl group.

17. The organic light-emitting device according to claim 10, wherein $R^1$ to $R^{15}$ that do not represent a halogen atom or an alkyl group represent hydrogen atoms.

18. The organic light-emitting device according to claim 10, wherein the organic light-emitting device emits delayed fluorescent light.

19. The organic light-emitting device according to claim 10, wherein the organic light-emitting device is an organic electroluminescent device.

20. The organic light-emitting device according to claim 19, wherein the organic light-emitting device comprises a pair of electrodes, and an organic layer including a light-emitting layer provided between the pair of electrodes, and
the compound represented by the general formula (1) is contained at least in the light-emitting layer.

21. The organic light-emitting device according to claim 1, wherein the compound has a fluorescence lifetime of 1 μs or less.

* * * * *